US007812150B2

(12) United States Patent
Constien et al.

(10) Patent No.: US 7,812,150 B2
(45) Date of Patent: Oct. 12, 2010

(54) RNAI MODULATION OF AHA AND THERAPEUTIC USES THEREOF

(75) Inventors: Rainer Constien, Kulmbach (DE); Birgit Bramlage, Kulmbach (DE); Pamela Tan, Kulmbach (DE); Hans-Peter Vornlocher, Bayreuth (DE); William Balch, San Diego, CA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 179 days.

(21) Appl. No.: 11/750,553

(22) Filed: May 18, 2007

(65) Prior Publication Data
US 2008/0113931 A1 May 15, 2008

Related U.S. Application Data

(60) Provisional application No. 60/801,840, filed on May 19, 2006.

(51) Int. Cl.
C07H 21/04 (2006.01)
(52) U.S. Cl. .................................................. 536/24.5
(58) Field of Classification Search ........................ None
See application file for complete search history.

(56) References Cited

U.S. PATENT DOCUMENTS

| 5,034,506 | A | 7/1991 | Summerton et al. |
| 5,139,941 | A | 8/1992 | Muzyczka et al. |
| 5,252,479 | A | 10/1993 | Srivastava |
| 5,264,221 | A | 11/1993 | Tagawa et al. |
| 5,328,470 | A | 7/1994 | Nabel et al. |
| 5,602,240 | A | 2/1997 | De Mesmaeker et al. |
| 5,665,710 | A | 9/1997 | Rahman et al. |
| 5,705,188 | A | 1/1998 | Junichi et al. |
| 6,054,299 | A | 4/2000 | Conrad |
| 6,071,497 | A | 6/2000 | Steiner et al. |
| 6,294,153 | B1 | 9/2001 | Modi |
| 6,344,194 | B1 | 2/2002 | Sene et al. |
| 6,747,014 | B2 | 6/2004 | Teng et al. |
| 6,887,906 | B1 | 5/2005 | Teng et al. |
| 2005/0255487 | A1* | 11/2005 | Khvorova et al. ............... 435/6 |
| 2007/0031844 | A1* | 2/2007 | Khvorova et al. ............... 435/6 |
| 2008/0113931 | A1 | 5/2008 | Constien et al. |

FOREIGN PATENT DOCUMENTS

| DE | 101 00 586 | 4/2002 |
| WO | WO 93/24641 | 12/1993 |
| WO | WO 94/13788 | 6/1994 |
| WO | WO 96/40062 | 12/1996 |
| WO | WO 97/04787 | 3/1997 |
| WO | WO 97/30731 | 8/1997 |
| WO | WO 99/32619 | 7/1999 |
| WO | WO 99/53050 | 10/1999 |
| WO | WO 99/61631 | 12/1999 |
| WO | WO 00/22113 | 4/2000 |
| WO | WO 00/22114 | 4/2000 |
| WO | WO 00/44895 | 8/2000 |
| WO | WO 00/50050 | 8/2000 |
| WO | WO 00/66206 | 11/2000 |
| WO | WO 01/60420 | 8/2001 |
| WO | WO 02/053190 | 7/2002 |
| WO | WO 02/066078 | 8/2002 |
| WO | WO 03/067262 | 8/2003 |
| WO | WO 03/070918 A | 8/2003 |
| WO | WO 2005/044981 A | 5/2005 |

OTHER PUBLICATIONS

Vickers et al. (2003) JBC 278:7108-7118.*
Holen et al. (2002) Nucleic Acids Res. 30:1757-1766.*
PCT International Search Report and Written Opinion, PCT/US2007/069229, Sep. 2, 2008, 9 Pages.
Allen, T.M., and Chonn, A., "Large Unilamellar Liposomes eith Low Uptake into the Reticuloendothelial System," *FEB* 223: 42-46 (1987).
Anderson, W. F., "Human Gene Therapy," *Nature* 392:25-30 (1998).
Berkner et al., "Development of Adenovirus Vectors for the Expression of Heterologous Genes," *Biotechniques*, 6: 616-629 (1988).
Bucchini et al., "Pancreatic Expression of Human Insulin Gene in Transgenic Mice," *Proc. Natl. Acad. Sci. USA*, 83:2511-2515 (1986).
Chen et al., "Gene Therapy for Brain Tumors: Regression of Experimental Gliomas by Adenovirus-Mediated Gene Transfer in vivo," *Proc. Natl. Acad. Sci. USA*, 91:3054-3057 (1994).
Cone et al., "High Efficiency Gene Transfer into Mammalian Cells: Generation of Helper-Free Recombinant Retrovirus with Broad Mammalian Host Range," *Proc. Natl. Acad. Sci. USA*, 81: 6349-6353 (1984).
Constantinides et al., "Formulation and Intestincal Absorption Enhancement Evaluation of Water-In-Oil Microemulsions Incorporating Medium-Chain Glycerides," *Pharmaceutical Research*, 11: 1385-1390 (1994).
Cornetta et al., "Safety Issues Related to Retroviral-Mediated Gene Transfer in Humans," *Human Gene Therapy*, 2:5-14 (1991).
Couture et al., "Anti-Gene Therapy: The Use of Ribozymes to Inhibit Gene Function," *TIG*, 12: 510-515 (1996).
Dai et al., "HSP90: A Rising Star on the Horizon of Anticancer Targets," *Future Oncol.*, 4: 529-540 (2005).
Docherty et al., "Nutrient Regulation of Insulin Gene Expression," *FASEB*, 8: 20-27 (1994).
Dornburg R., "Reticuloendotheliosis Viruses and Dervied Vectors," *Gene Therapy*, 2: 301-310 (1995).

(Continued)

*Primary Examiner*—Louis Wollenberger
(74) *Attorney, Agent, or Firm*—Fenwick & West LLP

(57) ABSTRACT

The invention relates to a double-stranded ribonucleic acid (dsRNA) for inhibiting the expression of an Aha gene (Aha1 gene), comprising an antisense strand having a nucleotide sequence which is less that 30 nucleotides in length, generally 19-25 nucleotides in length, and which is substantially complementary to at least a part of an Aha gene. The invention also relates to a pharmaceutical composition comprising the dsRNA together with a pharmaceutically acceptable carrier, methods for treating diseases caused by Aha1 expression and the expression of an Aha gene using the pharmaceutical composition; and methods for inhibiting the expression of an Aha gene in a cell.

14 Claims, No Drawings

OTHER PUBLICATIONS

Du Plessis et al., "Topical Delivery of Liposomally Encapsulated Gamma-Interferon," *Antiviral Research*, 18: 259-265 (1992).

Eglitis et al., "Retroviral Vecotrs for Introduction of Genes into Mammalian Cells," *Biotechniques*, 6: 608-614 (1988).

Fisher et al., "Transduction with Recombinant Adeno-Associated Virus for Gene Therapy is Limited by Leading-Strand Synthesis," *Journal of Virology*, 70:520-532 (1996).

Gassmann et al., "Maintenance of an Extrachromosomal Plasmid Vector in Mouse Embryonic Stem Cells," *Proc. Natl. Acad. Sci. USA*, 92: 1292-1296 (1995).

Ho et al., "Preparation and Microemulsions Using Polyglycerol Fatty Acid Esters as Surfactant for the Delivery of Protein Drugs," *Journal of Pharmaceutical Sciences*, 85: 138-143 (1996).

Hsu et al., "Immunogenicity of Recombinant Adenovirus-Respiratory Syncytial Virus Vaccines with Adenovirs Types 4, 5, and 7 Vectors in Dogs and Chimpanzees," *The Journal of Infectious Diseases*, 166: 769-775 (1992).

Hu et al., "Topical Delivery of Cyclosporin A from Non-Ionic Liposomal Systems: An in vivo/in vitro Correlation Study Using Hairless Mouse Skin," *S.T.P. Pharma Science*,4: 466-469 (1994).

Lotz et al., "Aha1 Binds to the Middle Domain of Hsp90, Contributes to Client Protein Activation, and Stimulated the ATPase Activity of the Molecular Chaperone," *The Journal of Biological Chemistry*, 278: 17228-17235 (2003).

Meyer et al., "Structural Basis for Recruitment of the ATPase Activator Aha1 to the Hsp90 Chaperone Machinery," *The EMBO Journal*, 23: 511-519 (2004).

Miller A.D., "Retrovirus Packaging Cells," *Human Gene Therapy*, 1: 5-14 (1990).

Miyao et al., "Stability and Pharmacokinetic Characteristics of Oligonucleotides Modified at Terminal Linkages in Mice," *Antisense Research and Development*, 5: 115-121 (1995).

Muzyczka, N., "Use of Adeno-Associated Virus as a General Transduction Vector for Mammalian Cells," *Current Topics in Microbiology and Immunology*, 158: 97-129 (1992).

Panaretou et al., "Activation of the ATPase Activity of Hsp90 by the Stress-Regulated Cochaperone Aha1," *Molecular Cells* 10: 1307-1318 (2002).

Panaretou et al., "ATP Binding and Hydrolysis are Essential to the Function of the Hsp90 Molecular Chaperone in vivo," *The EMBO Journal*, 17: 4829-4836 (1998).

Pearl et al., "Structure, Function, and Mechanism of the Hsp90 Molecular Chaperone," *Advances in Protein Chemistry*, 59 157-185 (2002).

Picard D., "Heat-Shock Protein 90, A Chaperone for Folding and Regulation," *Cell. Mol. Life Sci.*, 59: 1640-1648 (2002).

Pratt et al., "Regulation of Signaling Protein Function and Trafficking by the hsp90/hsp70-Based Chaperone Machinery," *Exp. Biol. Med.* 228: 111-133 (2003).

Pratt W.B., "The Role of the hsp90-Based Chaperone System in Signal Transduction by Nuclear Receptors and Receptors Signaling via Map Kinase,"*Annu. Rev. Pharmacol. Toxicol.*, 37: 297-326 (1997).

Prodromou et al., "Structure and Functional Relationships of Hsp90," *Current Cancer Drug Targets*, 3: 301-323 (2003).

Prodromou et al., "The ATPase Cycle of Hsp90 Drives a Molecular 'Clamp' Via Transient Dimerization of the N-Terminal Domains," *The EMBO Journal*, 19:4383-4392 (2000).

Rabinowitz et al., "Cross-Packaging of a Single Adeno-Associated Virus (AAV) Type 2 Vecotr Genome into Multiple AAV Serotypes Enables Transduction with Broad Specificity," *Journal of Virology*, 76: 791-801 (2002).

Ritschel W.A., "Microemulsions for Improved Peptide Absorption from the Gastrointestinal Tract," *Meth. Find. Exp. Clin. Phramacol.*, 13: 205-220 (1991).

Rosenfeld et al., "Adenovirus-Mediated Transfer of a Recombinant #1-Antitrypsin Gene to the Lung Epithelium in Vivo," *Science*, 252: 431-434 (1991).

Rosenfeld et al., "In Vivo Transfer of the Human Cystic Fibrosis Transmembrane Conductance Regulator Gene to the Airway Epithelium," *Cell*, 68:143-155 (1992).

Rubinson et al., "A Lentivirus-Based System to Functionally Silence Genes in Primary Mammalian Cells, Stem Cells and Transgenic Mice by RNA Interference," *Nature Genetics*, 33: 401-407 (2003).

Samulski et al., "A Recombinant Plasmid from Which an Infectious Aden-Associated Virus Genome Can be Excised in Vitro and its Use to Study Viral Replication," *Journal of Virology*, 61:3096-3101 (1987).

Samulski et al., "Helper-Free Stocks of Recombinant Adeno-Associated Viruses: Normal Integration Does Not Require Viral Gene Expression," *Journal of Virology*, 63: 3822-3828 (1989).

Sandrasagra et al., "Discovery and Development of Respirable Antisense Therapeutics for Asthma," *Antisense & Nucleic Acid Drug Development*, 12:177-181 (2002).

Sandrasagra et al., "RASONs: A Novel Antisense Olignucleotide Therapeutic Approach for Asthma," *Expert Opin. Biol. Ther*. 1:979-983 (2001).

Takakura et al., "Uptake Characteristics of Oligonucleotides in the Isolated Rat Liver Perfusion System," *Antisense & Nucleic Acid Drug Development*, 6: 177-183 (1996).

Templin et al., "Pharmacokinetic and Toxicity Profile of a Phosphorothioate Oligonucleotide Following Inhalation Delivery to Lung in Mice," *Antisense & Nucleic Acid Drug Development*, 10:359-368 (2000)Nov. 13, 2007.

Wang et al., "Plasmid DNA Adsorbed to pH-Sensitive Liposomes Efficiently Transforms the Target Cells," *Biochemical and Biophysical Research Communications*, 147: 980-985 (1987).

Weiner et al., "Liposomes: A Novel Topical Delivery System for Pharmaceutical and Cosmetic Applications," *Journal of Drug Targeting*, 2: 405-410 (1994).

Wu et al., "Increased Micorvascular Permeability Contributed to Preferential Accumulation of Stealth Liposome in Tumor Tissue," *Cancer Research*, 53:3765-3770 (1993).

Xia et al., "siRNA-Mediated Gene Silencing in vitro and in vivo," (2002) Nat. Biotechnol. 20:1006-1010.

Yang et al., "Evidence that Processed Small dsRNAs May Mediate sequence-specific mRNA Degradation during RNAi in *Drosophilia* Embryos," *Current Biology* 10:1191-1200 (2000).

Zhou et al., "Targeted Delivery DNA by Liposomes and Polymers," *Journal of Controlled Release*, 19: 269-274 (1992).

GenBank Accession No. NM_012111.1, (Priority Date: Feb. 24, 2007); 4 pages.

GenBank Accession No. NM_146036.1, (Priority Date: Mar. 2, 2007); 3 pages.

GenBank Accession No. NM_172391.3, (Priority Date: Apr. 27, 2007); 4 pages.

GenBank Accession No. NM_152392.1, (Priority Date: Apr. 6, 2007); 3 pages.

GenBank Accession No. XM_510094.1, (Priority Date: Sep. 15, 2006); 2 pages.

GenBank Accession No. XM_223680.3, (Priority Date: Jun. 22, 2006); 2 pages.

European Search Report for European Patent Application No. 07797577.9, Sep. 30, 2009, 22 Pages.

Harst, A., et al., "Aha1 competes with Hop, p50 and p23 for binding to the molecular chaperone Hsp90 and contributes to kinase and hormone receptor activation," The Biochemical Journal, May 1, 2005, pp. 789-796, vol. 387.

Harborth, J., et al., "Sequence, Chemical, and Structural Variation of Small Interfering RNA's and Short Hairpin RNAs and the Effect on Mammalian Gene Silencing," Antisense and Nucleic Acid Drug Development, 2003, pp. 83-105, vol. 13.

* cited by examiner

RNAI MODULATION OF AHA AND THERAPEUTIC USES THEREOF

CROSS-REFERENCE TO RELATED APPLICATION

This application claims the benefit of U.S. Provisional Application No. 60/801,840, filed May 19, 2006, which is hereby incorporated by reference in its entirely.

GOVERNMENT SUPPORT

The work described herein was carried out, at least in part, using funds from the United States government provided under the National Institutes of Health Grant No. GM 42336 and GM 45678/NIH RR 11823. The U.S. government may therefore have certain rights in the invention.

FIELD OF THE INVENTION

The present invention concerns methods of treatment using modulators of the gene Activator of Beat Shock Protein 90 ATPase (Aha). More specifically, the invention concerns methods of treating disorders associated with undesired Aha activity, by administering short interfering RNA which down-regulate the expression of Aha, and agents useful therein.

BACKGROUND OF THE INVENTION

Activator of Heat Shock Protein 90 ATPase 1 (herein: Aha1) is an activator of the ATPase-activity of Hsp90 and is able to stimulate the inherent activity of yeast Hsp90 by 12-fold and human Hsp90 by 50-fold (Panaretou, B., et al., Mol. Cell 2002, 10:1307-1318). Biochemical studies have shown that Aha1 binds to the middle region of Hsp90 (Panaretou et al. 2002, supra, Lotz, G. P., et al., J. Biol. Chem. 2003, 273; 17228-17235), and recent structural studies of the Aha1-Hsp90 core complex suggest that the co-chaperone promotes a conformational switch in the middle segment catalytic loop (370-390) of Hsp90 that releases the catalytic Arg380 and facilitates its interaction with ATP in the N-terminal nucleotide-binding domain (Meyer, P., et al., EMBO J. 2000, 23:511-519).

The molecular chaperons Heat shock protein 90 (Hsp90) is responsible for the in vivo activation or maturation of specific client proteins (Picard, D., Cell Mol. Life Sci. 2002, 59:1640-1648; Pearl, L. H., and Prodromou, C., Adv. Protein Chem. 2002, 59:157-185; Pratt, W. B., and Toft, D. O., Exp. Biol. Med. 2003, 228-111-133; Prodromou, C., and Pearl, L, H., Curr. Cancer Drug Targets 2003, 3:301-323). Crucial to such activation is the essential ATPase activity of Hsp90 (Panaretou, B., et al, EMBO J. 1998, 17:4829-4836), which drives a conformational cycle involving transient association of the N-terminal nucleotide-binding domains within the Hsp90 dimer (Prodromou, C., et al, EMBO J. 2000, 19:4383-4392).

As a molecular chaperone, HSP90 promotes the maturation and maintains the stability of a large number of conformationally labile client proteins, most of which are involved in biologic processes that are often deranged within tumor cells, such as signal transduction, cell-cycle progression and apoptosis. As a result, and in contrast to other molecular targeted therapeutics, inhibitors of HSP90 achieve promising anticancer activity through simultaneous disruption, of many oncogenic substrates within cancer cells (Whitesell L, and Dai C., Future Oncol. 2005; 1:529-540; WO 03/067262). Furthermore, HSP90 has been implicated in the degradation of Cystic Fibrosis Transmembrane Conductance Regulator (CFTR), Mutations in the CFTR gene lead to defective folding and ubiquination of the protein as a consequence of HSP90 ATPase activity. Following ubiquitination, CFTR is degraded before it can reach its site of activity. Lack of active CFTR then leads to the development of cystic fibrosis in human subjects having such mutation. Therefore, the inhibition of HSP90 activity may be beneficial for subjects suffering from cancer or Cystic Fibrosis.

Hsp90 constitutes about 1-2% of total cellular protein (Pratt, W. B., Annu. Rev. Pharmacol Toxicol. 1997, 37:297-326), and the inhibition of such large amounts of protein by means of an antagonist or inhibitor would potentially require the introduction of excessive amounts of the inhibitor or antagonist into a cell. An alternative approach is the inhibition of activators of HSP90's ATPase activity, such as Ana1, which are present in smaller amounts. By downregulating the amount of Aha1 present in the cell the activity of HSP90 may be lowered substantially.

Significant sequence homology exists between *Homo sapiens* (NM_01211.1), *Mus musculus* (NM_146036.1) and *Pan troglodytes* (XM_510094.1) Aha 1. A clear *rattus norvegicus* homologue of Aha 1 has not been identified; however, there is a *Rattus norvegicus* (XM_223680.3) gene which has been termed activator of heat shock protein. ATPase homolog 2 (Ahsa 2) on the basis of its sequence homology to yeast Ahsa 2. Its sequence is homologous to *mus musculus* RIKEN cDNA 1110064P04 gene (NM_172391.3), which is in turn similar in sequence to *Aus musculus* Aha 1 except for N-terminal truncation. A *homo sapiens* Ahsa 2 (NM_152392.1) has also been predicted, but sequence homology is limited. The functions of these latter three genes have not been sufficiently elucidated. However, there exists one region in which all of the above sequences are identical, and which may be used as the target for RNAi agents. It may be advantageous to inhibit the activity of more than one Aha gene.

Recently, double-stranded RNA molecules (dsRNA) have been shown to block gene expression in a highly conserved regulatory mechanism known as RNA interference (RNAi), WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., Curr. Biol. (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of pathological processes mediated by HSP90, there remains a need for an agent that can selectively and efficiently attenuate HSP90 ATPase activity using the cell's own RNAi machinery. Such agent shall possess both high biological activity and in vivo stability, and shall effectively inhibit expression of a target Aha gene, such as Aha1, for use in treating pathological processes mediated directly or indirectly by Aha expression, e.g. Aha1 expression.

SUMMARY OF THE INVENTION

The invention provides double-stranded ribonucleic acid (dsRNA), as well as compositions and methods for inhibiting the expression of an Aha gene in a cell or mammal using such dsRNA. The invention also provides compositions and methods for treating pathological conditions and diseases mediated by the expression of an Aha gene, such as in cancer or cystic fibrosis. The dsRNA of the invention comprises an RNA strand (the antisense strand) having a region which is less than 30 nucleotides in length, generally 19-24 nucleotides in length, and is substantially complementary to at least part of an mRNA transcript of an Aha gene.

In one aspect, the invention provides doable-stranded ribonucleic acid (dsRNA) molecules for inhibiting the expression of an Aha gene. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding ah Aha gene, and the region of complementarity is less than 30 nucleotides in length, generally 19-24 nucleotides in length. The dsRNA effects cleavage of an mRNA encoding an Aha gene within the target sequence of a second dsRNA having a sense strand chosen front the group of SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 43, SEQ ID NO: 43, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 1.11, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 1.45, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, and SEQ ID NO: 183, and an antisense strand complementary to the latter sense strand and chosen from the group of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, and SEQ ID NO: 184 (see Table 1 and Table 2). The Aha gene is preferably an Aha1 gene, and more preferably a *Homo sapiens* Aha1 gene. The dsRNA, upon contacting with a cell expressing the Aha gene, may is inhibit the expression of the Aha gene in said cell by at least 20%, or at least 25%, 30%, 35%, 40%, 45%, 50%, 55% 60%, 65%, 70%, 85%, 90% or 95%, e.g. in HeLa and/or MLE 12 cells. The dsRNA may be different from said second dsRNA, but may have at least 5, at least 10, at least 15, at least 18, or at least 20 contiguous nucleotides per strand in common with one of the above named nucleotide sequences.

Preferably, the second dsRNA is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-73.23, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-BP-9284, AL-DP-9285, AL-DP-9286, AL-DP-9287, AL-DP-9288, and AL-DP-9289 (see Table 1 and Table 2).

Alternatively, the dsRNA itself may be chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL DP-7312, AL-DP-7339, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289 (see Table 1 and Table 2).

The dsRNA may comprise at least one modified nucleotide. Preferably, the modified nucleotide is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, the modified nucleotide is chosen from the group of; a 2'-deoxy-2'-fluoro modified nucleotide, a 2'-deoxy-modified nucleotide, a locked nucleotide, an a basic nucleotide, 2'-amino-modified nucleotide, 2'-alkyl-modified nucleotide, morpholino nucleotide, a phosphoramidate, and a non-natural base comprising nucleotide.

In another aspect, the invention provides an isolated cell composing one of the dsRNAs of the invention. The cell is generally a mammalian cell, such as a human cell. Other embodiments of the cell comprising a dsRNA of the invention are as provided for other aspects of the invention above.

In yet another aspect, a pharmaceutical composition for inhibiting the expression of an Aha gene in an organism is provided, comprising a dsRNA and a pharmaceutically acceptable carrier, wherein the dsRNA comprises at least two sequences that are complementary to each other and wherein a sense strand comprises a first sequence and an antisense strand comprises a second sequence comprising a region of complementarity which is substantially complementary to at least a part of a mRNA encoding an Aha gene, and wherein said region of complementarity is less than 30 nucleotides in length, and wherein the dsRNA effects cleavage of an mRNA encoding an Aha gene within the target sequence of a second dsRNA having a sense strand chosen from the group of SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, and SEQ ID NO: 183, and an antisense strand complementary to the latter sense strand and chosen from the group of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ CD NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180. SEQ ID NO: 182, and SEQ ID NO: 184 (see Table 1 and Table 2). Therein, the Aha gene may be an Aha1 gene, and preferably a *Homo sapiens* Aha1 gene. The dsRNA comprised in the pharmaceutical composition may, upon contact with a cell expressing said Aha gene. Inhibit the expression of said Aha gene in said cell by at least 20%, or at least 25%, 30%, 35%, 40%, 45%, 50%, 55% 60%, 65%, 70%, 85%, 90% or 95%, e.g. in HeLa and/or MLE 12 cells. The dsRNA may be different from said second dsRNA, hot may have at least 5, at least 10, at least 15, at least 18, or at least 20 contiguous nucleotides per strand in common with one of the above named nucleotide sequences.

Preferably, the second dsRNA is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AD-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289 (see Table 1 and Table 2).

Alternatively, the dsRNA comprised in the pharmaceutical composition itself may be chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-7323, AL-DP-7335, AL-DP-7338, AL-BP-7341, AL-DP-7302, AL-DP-7315, AL-DP-7328, AL-DP-7330, AL-DP-7336, AL-DP-7348, AL-DP-9250, AL-DP-9251, AL-DP-9252, AL-DP-9253, AL-DP-9254, AL-PP-9255, AL-DP-9256, AL-DP-9257, AL-DP-9258, AL-DP-9259, AL-DP-9260, AL-DP-9261, AL-DP-9262, AL-DP-9263, AL-DP-0264, AL-DP-9265, AL-BP-9266, AL-DP-9267, AL-DP-9268, AL-DP-9269, AL-DP-9270, AL-DP-9271, AL-DP-9272. AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289 (see Table 1 and Table 2).

The dsRNA comprised in the pharmaceutical composition may comprise at least one modified nucleotide. Preferably, said modified nucleotide is chosen from the group of; a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide is chosen from the group of; a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

In yet another aspect, a method for inhibiting the expression of an Aha gene in a cell is provided, the method comprising:

(a) introducing into the cell a double-stranded ribonucleic acid (dsRNA), wherein the dsRNA comprises at least two sequences that are complementary to each other and wherein a sense strand comprises a first sequence and an antisense strand comprises a second sequence comprising a region of complementarity which is substantially complementary to at least a part of a mRNA encoding Aha1, and wherein said region of complementarity is less than 30 nucleotides in length and wherein the dsRNA effects cleavage of an mRNA encoding an Aha gene within the target sequence of a second dsRNA having a sense strand chosen from the group of SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133. SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, and SEQ ID NO: 183, and an antisense strand complementary to the latter sense strand and chosen from the group of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 7.8, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, and SEQ ID NO: 184; and (b) maintaining the cell produced in step (a) for a time sufficient to obtain degradation, of the mRNA transcript, of an Aha gene, thereby inhibiting expression of an Aha gene in the cell. The Aha gene is preferably an Aha1 gene, and more preferably a *homo sapiens* Aha1 gene. The dsRNA may be different from said second dsRNA, but may have at least 5, at least 10, at least 15, at least 18, or at least 20 contiguous nucleotides per strand In common with one of the above named nucleotide sequences.

Preferably, the second dsRNA is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-7323, AL-DP-7333, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9234, AL-DP-9285, AL-DP-9286, AL-DP-9287, AL-DP-9288, and AL-DP-9289 (see Table 1 and Table 2).

Alternatively, the dsRNA itself is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340. AL-DP-7342, AL-DP-7303, AL-DP-7305, AL-DP-7307, AL-DP-7309, AL-DP-7316, and AL-DP-7337, AL-DP-7304, AL-DP-7312, AL-DP-339, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9283, and AL-DP-9289. Preferably, the method is performed in vitro. Other embodiments of the method for inhibiting the expression of an Aha gene in a cell are as provided for other aspects of the invention above.

In yet another aspect, a method of treating, preventing or managing pathological processes mediated by Aha expression is provided, comprising administering to a patient in need of such treatment, prevention or management a therapeutically or prophylactically effective amount of a dsRNA, wherein the dsRNA comprises at least two sequences that are complementary to each other and wherein a sense strand comprises a first sequence and an antisense strand comprises a second sequence comprising a region of complementarity which is substantially complementary to at least a part of a mRNA encoding Aha1, and wherein said region of complementarity is less than 30 nucleotides in length and wherein the dsRNA effects cleavage of an mRNA encoding an Aha gene within the target sequence of a second dsRNA having a sense strand chosen from the group of SEQ ID NO: 5, SEQ ID NO: 7, SEQ ID NO: 9. SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 103, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, and SEQ ID NO: 183, and an antisense strand complementary to the latter sense strand and chosen from the group of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90. SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, and SEQ ID NO: 184. The dsRNA may be different from said second dsRNA, but may have at least 5, at least 10, at least 15, at least 18, or at least 20 contiguous nucleotides per strand in common with one of the above named nucleotide sequences.

Preferably, the second dsRNA is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AX-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289 (see Table 1 and Table 2).

Alternatively, the dsRNA itself is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289. Other embodiments of the method comprising administering a dsRNA of the invention are as provided for other aspects of the invention above.

In yet another aspect, a vector for inhibiting the expression of an Aha gene in a cell is provided, said vector comprising a regulatory sequence operably linked to a nucleotide sequence that encodes at least one strand of a dsRNA, wherein one of the strands of said dsRNA is substantially complementary to at least a part of a mRNA encoding Aha1 and wherein said dsRNA is less than 30 base pairs in length and wherein, the dsRNA effects cleavage of an mRNA encoding an Aha gene within the target sequence of a second dsRNA having a sense strand chosen from the group of SEQ ID NO: 5, SEQ ID NO: 7, SEQ ID NO: % SEQ ID NO: 11, SEQ ID NO: 13, SEQ ID NO: 15. SEQ ID NO: 17, SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 11.1, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, and SEQ ID NO: 183, and an antisense strand complementary to the latter sense strand and chosen from the group of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, and SEQ ID NO: 184. The dsRNA may be different from said second dsRNA, bid may have at least 5, at least 10, at least 15, at least 18, or at least 20 contiguous nucleotides per strand in common with one of the above named nucleotide sequences.

Preferably, the second dsRNA is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7320, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-7339, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-926, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289 (see Table 1 and Table 2). Other embodiments of the vector of the invention are as provided for other aspects of the invention above.

In yet another aspect, an isolated cell comprising the above vector is provided. Other embodiments of the cell comprising a vector of the invention are as provided for other aspects of the invention above.

TABLE 1

RNAi agents for the down-regulation of *homo sapiens* (NM_012111.1), *mus musculus* (NM_146036.1) and *pan troglodytes* (XM_510094.1) Aha 1, and minimal off-target interactions in rat cells; AL-DP-7561, AL-DP-7562, AL-DP-7563 and AL-DP-7564 are additionally cross-reactive to *mus musculus* (NM_172391.3) and *rattus norvegicus* (XM_223680.3) Aha 2

| Duplex identifier | Sense strand sequence[1] | SEQ ID NO: | Antisense strand sequence[1] | SEQ ID NO: |
|---|---|---|---|---|
| AL-DP-7299 | auugguccacggauaagcuTT | 1 | agcuuauccguggaccaauTT | 2 |
| AL-DP-7300 | gugaguaagcuugauggagTT | 3 | cuccaucaagcuuacucacTT | 4 |
| AL-DP-7301 | agucaaaauccccacuuguTT | 5 | acaagugggauuuugacuTT | 6 |
| AL-DP-7302 | aaaucucguggccuuaaugTT | 7 | cauuaaggccacgagauuuTT | 8 |
| AL-DP-7303 | gagauuagugugagccuugTT | 9 | caaggcucacacuaaucucTT | 10 |
| AL-DP-7304 | aaucucguggccuuaaugaTT | 11 | ucauuaaggccacgagauuTT | 12 |
| AL-DP-7305 | agauuagugugagccuugcTT | 13 | gcaaggcucacacuaaucuTT | 14 |
| AL-DP-7306 | cgggcggacgccaccaacgTT | 15 | cguugguggcguccgcccgTT | 16 |
| AL-DP-7307 | ggcggacgccaccaacgtcTT | 17 | gacguugguggcguccgccTT | 18 |
| AL-DP-7308 | gggcggacgccaccaacguTT | 19 | acguugguggcguccgcccTT | 20 |
| AL-DP-7309 | caacgucaacaacuggcacTT | 21 | gugccaguuguugacguugTT | 22 |
| AL-DP-7310 | gcgggcggacgccaccaacTT | 23 | guuggugguccgcccgcTT | 24 |

TABLE 1-continued

RNAi agents for the down-regulation of *homo sapiens* (NM_012111.1), *mus musculus* (NM_146036.1) and *pan troglodytes* (XM_510094.1) Aha 1, and minimal off-target interactions in rat cells; AL-DP-7561, AL-DP-7562, AL-DP-7563 and AL-DP-7564 are additionally cross-reactive to *mus musculus* (NM_172391.3) and *rattus norvegicus* (XM_223680.3) Aha 2

| Duplex identifier | Sense strand sequence[1] | SEQ ID NO: | Antisense strand sequence[1] | SEQ ID NO: |
|---|---|---|---|---|
| AL-DP-7311 | aucucguggccuuaaugaaTT | 25 | uucauuaaggccacgagauTT | 26 |
| AL-DP-7312 | acgucaacaacuggcacugTT | 27 | cagugccaguuguugacguTT | 28 |
| AL-DP-7313 | accaacgucaacaacuggcTT | 29 | gccaguuguugacguuggTT | 30 |
| AL-DP-7314 | acgcuggaucguggaggagTT | 31 | cuccuccacgauccagcguTT | 32 |
| AL-DP-7315 | agacccacgcuggaucgugTT | 33 | cacgauccagcguggucuTT | 34 |
| AL-DP-7316 | gacccacgcuggaucguggTT | 35 | ccacgauccagcguggucTT | 36 |
| AL-DP-7317 | gaauuuacaucagcacccuTT | 37 | agggugcugauguaaauucTT | 38 |
| AL-DP-7318 | gggaauuuacaucagcaccTT | 39 | ggugcugauguaaauucccTT | 40 |
| AL-DP-7319 | ugggaauuuacaucagcacTT | 41 | gugcugauguaaauucccaTT | 42 |
| AL-DP-7320 | ccaacgucaacaacuggcaTT | 43 | ugccaguuguugacguuggTT | 44 |
| AL-DP-7321 | aagugggugagggagaccTT | 45 | ggucccucaccccacuuTT | 46 |
| AL-DP-7322 | acacaaaucucguggccuuTT | 47 | aaggccacgagauuuguguTT | 48 |
| AL-DP-7323 | acccacgcuggaucguggaTT | 49 | uccacgauccagcguggguTT | 50 |
| AL-DP-7324 | gagucaaaaucccacuugTT | 51 | caagugggggauuuugacucTT | 52 |
| AL-DP-7325 | gagcucuauagaguguuuaTT | 53 | uaaacacucuauagagcucTT | 54 |
| AL-DP-7326 | ggcagcgguacuacuuugaTT | 55 | ucaaaguaguaccgcugccTT | 56 |
| AL-DP-7327 | gacacaaaucucguggccuTT | 57 | aggccacgagauuugugucTT | 58 |
| AL-DP-7328 | agcgggcggacgccaccaaTT | 59 | uugguggcguccgcccgcuTT | 60 |
| AL-DP-7329 | caaaaucccacuuguaagTT | 61 | cuuacaaguggggauuuugTT | 62 |
| AL-DP-7330 | gagacccacgcuggaucguTT | 63 | acgauccagcguggucucTT | 64 |
| AL-DP-7331 | gagccuugccaaagaugagTT | 65 | cucaucuuuggcaaggcucTT | 66 |
| AL-DP-7332 | ugacacaaaucucguggccTT | 67 | ggccacgagauuugugucaTT | 68 |
| AL-DP-7333 | ggagcucuauagaguguuuTT | 69 | aaacacucuauagagcuccTT | 70 |
| AL-DP-7334 | cccacgcuggaucguggagTT | 71 | cuccacgauccagcgugggTT | 72 |
| AL-DP-7335 | gaucccaauuugucugauTT | 73 | aucagacaaauuggggaucTT | 74 |
| AL-DP-7336 | gagaucccaauuugucugTT | 75 | cagacaaauuggggaucucTT | 76 |
| AL-DP-7337 | agccugacacaaaucucguTT | 77 | acgagauuugugucaggcuTT | 78 |
| AL-DP-7338 | agaucccaauuugucugaTT | 79 | ucagacaaauuggggaucuTT | 80 |
| AL-DP-7339 | agggagacccacgcuggauTT | 81 | auccagcguggucucccuTT | 82 |
| AL-DP-7340 | gagggagacccacgcuggaTT | 83 | uccagcguggucuccccucTT | 84 |
| AL-DP-7341 | gccaagugggugagggagTT | 85 | cucccucaccccacuuggcTT | 86 |
| AL-DP-7342 | uggcagcgguacuacuuugTT | 87 | caaaguaguaccgcugccaTT | 88 |
| AL-DP-7343 | ugagggagacccacgcuggTT | 89 | ccagcguggucucccucaTT | 90 |

TABLE 1-continued

RNAi agents for the down-regulation of *homo sapiens* (NM_012111.1), *mus musculus* (NM_146036.1) and *pan troglodytes* (XM_510094.1) Aha 1, and minimal off-target interactions in rat cells; AL-DP-7561, AL-DP-7562, AL-DP-7563 and AL-DP-7564 are additionally cross-reactive to *mus musculus* (NM_172391.3) and *rattus norvegicus* (XM_223680.3) Aha 2

| Duplex identifier | Sense strand sequence[1] | SEQ ID NO: | Antisense strand sequence[1] | SEQ ID NO: |
|---|---|---|---|---|
| AL-DP-7344 | aguggagauuagugugagcTT | 91 | gcucacacuaaucuccacuTT | 92 |
| AL-DP-7345 | aggagcucuauagaguguuTT | 93 | aacacucuauagagcuccuTT | 94 |
| AL-DP-7346 | agcgguacuacuuugagggTT | 95 | cccucaaaguaguaccgcuTT | 96 |
| AL-DP-7561 | cgcuggaucguggaggagcTT | 97 | gcuccuccacgauccagcgTT | 98 |
| AL-DP-7562 | gcuggaucguggaggagcgTT | 99 | cgcuccuccacgauccagcTT | 100 |
| AL-DP-7563 | cuggaucguggaggagcggTT | 101 | ccgcuccuccacgauccagTT | 102 |
| AL-DP-7564 | uggaucguggaggagcgggTT | 103 | cccgcuccuccacgauccaTT | 104 |

[1]Capital letters = desoxyribonucleotides; small letters = ribonucleotides

TABLE 2

RNAi agents for the down-regulation of *homo sapiens* (NM_012111.1), *mus musculus* (NM_146036.1) and *pan troglodytes* (XM_510094.1) Aha 1, and minimal off-target interactions in human cells

| Duplex identifier | Sense strand sequence[1] | SEQ ID NO: | Antisense strand sequence[1] | SEQ ID NO: |
|---|---|---|---|---|
| AL-DP-9250 | gccugacacaaaucucgugTT | 105 | cacgagauuugugucaggcTT | 106 |
| AL-DP-9251 | ccugacacaaaucucguggTT | 107 | ccacgagauuugugucaggTT | 108 |
| AL-DP-9252 | acgccaccaacgucaacaaTT | 109 | uuguugacguuggguggcguTT | 110 |
| AL-DP-9253 | agcucuauagaguguuuacTT | 111 | guaaacacucuauagagcuTT | 112 |
| AL-DP-9254 | gggcuggcagcgguacuacTT | 113 | guaguaccgcugccagcccTT | 114 |
| AL-DP-9255 | cuggcagcgguacuacuuuTT | 115 | aaaguaguaccgcugccagTT | 116 |
| AL-DP-9256 | ggaugaaguggagauuaguTT | 117 | acuaaucuccacuucauccTT | 118 |
| AL-DP-9257 | accagaggagcucuauagaTT | 119 | ucuauagagcuccucugguTT | 120 |
| AL-DP-9258 | aaguggagauuagugugagTT | 121 | cucacacuaaucuccacuuTT | 122 |
| AL-DP-9259 | gaggagcucuauagaguguTT | 123 | acacucuauagagcuccucTT | 124 |
| AL-DP-9260 | gggagacccacgcuggaucTT | 125 | gauccagcgugggucuccc TT | 126 |
| AL-DP-9261 | ugagccugacacaaaucucTT | 127 | gagauuugugucaggcucaTT | 128 |
| AL-DP-9262 | gcggacgccaccaacgucaTT | 129 | ugacguuggugcguccgcTT | 130 |
| AL-DP-9263 | cggacgccaccaacgucaaTT | 131 | uugacguuggugcguccgTT | 132 |
| AL-DP-9264 | gaaguggagauuagugugaTT | 133 | ucacacuaaucuccacuucTT | 134 |
| AL-DP-9265 | cucgguggccuuaaugaaggTT | 135 | ccuucauuaaggccacgagTT | 136 |
| AL-DP-9266 | ucgguggccuuaaugaaggaTT | 137 | uccuucauuaaggccacgaTT | 138 |
| AL-DP-9267 | aaugggaauuuacaucagcTT | 139 | gcugauguaaauucccauuTT | 140 |
| AL-DP-9268 | ggaauuuacaucagcaccc TT | 141 | gggugcugauguaaauuccTT | 142 |

TABLE 2-continued

RNAi agents for the down-regalation of homo sapiens (NM_012111.1), mus musculus (NM_146036.1) and pan troglodytes (XM_510094.1) Aha 1, and minimal off-target interactions in human cells

| Duplex identifier | Sense strand sequence[1] | SEQ ID NO: | Antisense strand sequence[1] | SEQ ID NO: |
|---|---|---|---|---|
| AL-DP-9269 | ggagauuagugugagccuuTT | 143 | aaggcucacacuaaucuccTT | 144 |
| AL-DP-9270 | cacaaaucucgugggccuuaTT | 145 | uaaggccacgagauuugugTT | 146 |
| AL-DP-9271 | acaaaucucguggccuuaaTT | 147 | uuaaggccacgagauuuguTT | 148 |
| AL-DP-9272 | ggagacccacgcuggaucgTT | 149 | cgauccagcgugggucuccTT | 150 |
| AL-DP-9273 | ggacgccaccaacgucaacTT | 151 | guugacguugguggcguccTT | 152 |
| AL-DP-9274 | gaugaaguggagauuagugTT | 153 | cacuaaucuccacuucaucTT | 154 |
| AL-DP-9275 | gugagccuugccaaagaugTT | 155 | caucuuuggcaaggcucacTT | 156 |
| AL-DP-9276 | caaugaauggagagucaguTT | 157 | acugacucuccauucauugTT | 158 |
| AL-DP-9277 | auuagugugagccuugccaTT | 159 | uggcaaggcucacacuaauTT | 160 |
| AL-DP-9278 | agaugagccugacacaaauTT | 161 | auuugugucaggcucaucuTT | 162 |
| AL-DP-9279 | uagugugagccuugccaaaTT | 163 | uuuggcaaggcucacacuaTT | 164 |
| AL-DP-9280 | uuugccaccaucaccuugaTT | 165 | uugaagcaucucucuccguTT | 166 |
| AL-DP-9281 | acggagagaugcuucaaTT | 167 | uugaagcaucucucuccguTT | 168 |
| AL-DP-9282 | cggagagagaugcuucaaaTT | 169 | uuugaagcaucucucuccgTT | 170 |
| AL-DP-9283 | aaaauccccacuuguaagaTT | 171 | ucuuacaagugggggauuuuTT | 172 |
| AL-DP-9284 | auccccaauuugucugaugTT | 173 | caucagacaaauugggauTT | 174 |
| AL-DP-9285 | ucaaaauccccacuuguaaTT | 175 | uuacaaguggggauuugaTT | 176 |
| AL-DP-9286 | aaauccccacuuguaagauTT | 177 | aucuuacaaguggggauuuTT | 178 |
| AL-DP-9287 | uccccaauuugucugaugaTT | 179 | ucaucagacaaauuggggaTT | 180 |
| AL-DP-9288 | auggccaagugggugaggTT | 181 | ccucaccccacuuggccauTT | 182 |
| AL-DP-9289 | ggagucaaaauccccacuuTT | 183 | aagugggggauuuugacuccTT | 184 |

[1]Capital letters = desoxyribonucleotides; small letters = ribonucleotides

BRIEF DESCRIPTION OF THE FIGURES

No Figures are presented.

DETAILED DESCRIPTION OF THE INVENTION

The invention provides doable-stranded ribonucleic acid (dsRNA) as well as compositions and methods for inhibiting the expression of an Aha gene in a cell or mammal using the dsRNA. The invention also provides compositions and methods for treating pathological conditions and diseases in a mammal caused by fee expression of an Aha gene using dsRNA. dsRNA directs the sequence-specific degradation of mRNA through a process known as RNA interference (RNAi).

The dsRNA of the invention comprises an RNA strand (the antisense strand) having a region which is less than 30 nucleotides in length, generally 19-24 nucleotides in length, and is substantially complementary to at least part of an mRNA transcript of an Aha gene. The use of these dsRNAs enables the targeted degradation of mRNAs of genes that are implicated in replication and or maintenance of cancer cells in mammals, and/or in the degradation of misfolded Cystic Fibrosis Transmembrane Conductance Regulator (CFTR). Using cell-based and animal assays, the present inventors have demonstrated that very low dosages of these dsRNA can specifically and efficiently mediate RNAi, resulting in significant inhibition of expression of an Aha gene. Thus, the methods and compositions of the invention comprising these dsRNAs are useful for treating pathological processes mediated by Aha expression, e.g. cancer and/or cystic fibrosis, by targeting a gene involved in protein degradation.

The following detailed description discloses how to make and use the dsRNA and compositions containing dsRNA to inhibit the expression of an Aha gene, as well as compositions and methods for treating diseases and disorders caused by the expression of an Aha gene, such as cancer and/or cystic fibrosis. The pharmaceutical compositions of the invention comprise a dsRNA having an antisense strand comprising a region of complementarity which is less than 30 nucleotides in length, generally 19-24 nucleotides in length, and is substantially complementary to at least part of an RNA transcript of an Aha gene, together with a pharmaceutically acceptable carrier.

Accordingly, certain aspects of the invention, provide pharmaceutical compositions comprising the dsRNA of the invention together with a pharmaceutically acceptable carrier, methods of using the compositions to inhibit expression of an Aha gene, and methods of using the pharmaceutical compositions to treat diseases caused by expression of an Aha gene.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A", "T" and "U" (irrespective of whether written in capital or small letters) each generally stand for a nucleotide that contains guanine, cytosine, adenine, thymine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, thymine, and uracil may be replaced by other moieties without substantially altering the base pairing properties of an oligonucleotide comprising a nucleotide hearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "Aha gene" refers to Activator of Beat Shock Protein 90 ATPase genes, "Aha1" refers to Activator of Heat Shock Protein 90 ATPase 1 genes, non-exhaustive examples of which are found under Genbank accession numbers NM_12111.1 (*Homo sapiens*), NM_146036.1 (*Mus musculus*), and XM_510094.1 (Pan troglodytes), "Aha2" refers to putative Activator of Heat Shock Protein 90 ATPase 2 genes, also known Ahsa1, non-exhaustive examples of which may be found under Genbank accession numbers N_72391.3 (*Mus musculus*) and XM_223680.3 (*Rattus norvegicus*).

As used herein, "target, sequence" refers to a contiguous portion of the nucleotide sequence of an mRNA molecule formed during the transcription of an Aha gene, including mRNA that is a product of RNA processing of a primary transcription product. The target sequence of any given RNAi agent of the invention means an mRNA-sequence of X nucleotides that is targeted by the RNAi agent by virtue of the complementarity of the antisense strand of the RNAi agent to such sequence and to which the antisense strand may hybridize when brought into contact with the mRNA, wherein X is the number of nucleotides in the antisense strand plus the number of nucleotides in a single-stranded overhang of the sense strand, if any.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and farm a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most, relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "Tally complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding Aha1). For example, a polynucleotide is complementary to at least apart, of an Aha1 mRNA if the sequence is substantially complementary to a non-interrupted portion of an mRNA encoding Aha1.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa, "Blunt" or "blunt end" means that there are no unpaired nucleotides at that end of the dsRNA, i.e., no nucleotide overhang. A "blunt ended" dsRNA is a dsRNA that has no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. Most preferably, the mismatches are located within 6, 5, 4, 3, or 2 nucleotides of the 5' terminus of the antisense strand and/or the 3' terminus of the sense strand.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is past of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to an Aha gene, e.g. an Aha1 gene, herein refer to the at least partial suppression of the expression of an Aha gene, e.g. an Aha1 gene, as manifested by a reduction of the amount of mRNA transcribed from an Aha gene which may be isolated from a first cell or group of cells in which an Aha gene is transcribed and which has or have been treated such that the expression of an Aha gene is inhibited, as compared to a second cell or group of cells substantially identical to the first cell or group of cells but which, has or have not been so treated (control cells). Preferably, the cells are HeLa or MLE 12 cells. The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Aha gene transcription, e.g. the amount of protein encoded by an Aha gene which is secreted by a cell, or found in solution after lysis of such cells, or the number of cells displaying a certain phenotype, e.g. apoptosis or cell surface CFTR. In principle, Aha gene silencing may be determined in any cell expressing the target, either constitutively or by genomic engineering, and by any appropriate assay. However, when a reference is needed in order to determine whether a given dsRNA inhibits the expression of an Aha gene by a certain degree and therefore is encompassed by the instant invention, the assays provided in the Examples below shall serve as such reference.

For example, in certain instances, expression of an Aha gene, e.g. an Aha1 gene, is suppressed by at least about 20%, 25%, 35%, or 50% by administration of the double-stranded oligonucleotide of the invention. In some embodiment, an Aha gene, e.g. an Aha1 gene, is suppressed by at least about 60%, 70%, or 80% by administration of the double-stranded oligonucleotide of the invention. In some embodiments, an Aha gene, e.g. an Aha1 gene, is suppressed by at least about 85%, 90%, or 95% by administration of the double-stranded oligonucleotide of the invention. Table 6 provides values for inhibition of Aha1 expression using various dsRNA molecules of the invention.

As used herein in the context of Aha expression, e.g. Aha1 expression, the tonus "treat", "treatment", and the like, refer to relief from or alleviation of pathological processes mediated by Aha expression. In the context of the present invention insofar as it relates to any of the other conditions recited herein below (other than pathological processes mediated by Aha expression), the terms "treat", "treatment", and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of pathological processes mediated by Aha expression or an overt symptom of pathological processes mediated by Aha expression. The specific amount that is therapeutically effective can be readily determined by ordinary medical practitioner, and may vary depending on factors known in the art, such as, e.g. the type of pathological processes mediated by Aha expression, the patient's history and age, the stage of pathological processes mediated by Aha expression, and the administration of other anti-pathological processes mediated by Aha expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

Double-Stranded Ribonucleic Acid (dsRNA)

In one embodiment, the invention provides doablestranded ribonucleic acid (dsRNA) molecules for inhibiting the expression of an Aha gene, e.g. an Aha1 gene, in a cell or mammal, wherein the dsRNA comprises an antisense strand comprising a region of complementarity which is complementary to at least a part of an mRNA formed in the expression of an Aha gene, e.g. an Aha1 gene, and wherein the region of complementarity is less than 30 nucleotides in length, generally 19-24 nucleotides in length. The dsRNA may be identical to one of the dsRNAs shown in Table 1 and Table 2, or it may effect cleavage of an mRNA encoding an Aha gene within the target sequence of one of the dsRNAs shown in Table 1 and Table 2. Preferably, the dsRNA has at least 5, at least 10, at least 15, at least 18, or at least 20 contiguous nucleotides per strand in common with at least one strand, but preferably both strands, of one of the dsRNAs shown in Table 1 and Table 2. Alternative dsRNAs that target elsewhere in the target sequence of one of the dsRNAs provided in Table 1 and Table 2 can readily be determined using the target sequence and the flanking Aha1 sequence.

The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of an Aha gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region, of complementarity to the target sequence is between 15 and 30, more generally between 18 and 25, yet more generally between 1.9 and 24, and most generally between 19 and 21 nucleotides in length. The dsRNA of the invention may further comprise one or more single-stranded nucleotide overhang(s). The dsRNA can be synthesized by standard methods known in fee art as further discussed below, e.g., by use of an automated DNA synthesizer, such as are commercially available from, for example, Biosearch, Applied Biosystems, inc. In a preferred embodiment, an Aha gene is the human Aha1 gene. In specific embodiments, the first strand of the dsRNA comprises the sense sequences of the RNAi agents AL-DP-7301-AL-DP-7346 and AL-DP-7561-AL-DP-7564 (Table 1), and AL-DP-9250-AL-DP-9289 (Table 2), and the second sequence is selected from the group consisting of the antisense sequences of AL-DP-7301-AL-DP-7346 and AL-DP-7561 AL-DP-7564 (Table 1), and AL-DP-9250-AL-DP-9289 (Table 2).

In further embodiments, the dsRNA comprises at least one nucleotide sequence selected from the groups of sequences provided above for the RNAi agents AL-DP-7301-AL-DP-7346 and AL-DP-7561-AL-DP-7564 (Table 1), and AL-DP-9250-AL-DP-9289 (Table 2). In other embodiments, the dsRNA comprises at least two sequences selected from this group, wherein one of the at least two sequences is complementary to another of the at least two sequences, and one of the at least two sequences is substantially complementary to a sequence of an mRNA generated in the expression of an Aha gene, e.g. an Aha1 gene. Generally, the dsRNA comprises two oligonucleotides, wherein one oligonucleotide may be described as the sense strand in one of the RNAi agents AL-DP-7301-AL-DP-7346 and AL-DP-7561-AL-DP-7564 (Table 1), and AL-DP-9250-AL-DP-9289 (Table 2), and the second oligonucleotide may be described as the antisense strand in one of the RNAi agents AL-DP-7301-AL-DP-7346 and AL-DP-7561-AL-DP-7564 (Table 1), and AL-DP-9250-AL-DP-9289 (Table 2).

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided for the RNAi agents AL-DP-7301-AL-DP-7346 and AL-DP-7561-AL-DP-7564 (Table 1), and AL-DP-9250-AL-DP-9289 (Table 2), the dsRNAs of the invention can comprise at least one strand of a length of minimally 21 nt. It can be reasonably expected that shorter dsRNAs comprising one of the sequences provided herein for the RNAi agents AL-DP-7301-AL-DP-7346 and AL-DP-7561-AL-DP-7564 (Table 1), and AL-DP-9250-AL-DP-9289 (Table 2), minus only a few nucleotides on one or both ends may be similarly effective as compared to the dsRNAs described above. Hence, dsRNAs comprising a partial sequence of at least 15, 16, 17, 13, 19, 20, or more contiguous nucleotides from one of the sequences of the RNAi agents AL-DP-7301-AL-DP-7346 and AL-DP-7561-AL-DP-7564 (Table 1), and AL-DP-9250-AL-DP-9289 (Table 2), and differing in their ability to inhibit the expression of an Aha gene, e.g. an Aha1 gene, in a FACS assay as described herein below by not more than 5, 10, 15, 20, 25, or 30% inhibition from a dsRNA comprising the full sequence, are contemplated by the invention.

Further dsRNAs that cleave within the target sequence of the RNAi agents AL-DP-7301-AL-DP-7346 and AL-DP-7561-AL-DP-7564 (Table 1), and AL-DP-9250-AL-DP-9289 (Table 2), can readily be made using the Aha1 gene sequence and the respective target sequence. The RNAi agents provided in Table 1 and Table 2 identify a site in the Aha1 mRNA that is susceptible to RNAi based cleavage. As such the present invention includes RNAi agents that target within the sequence targeted by one of the agents of the present invention. As used herein a dsRNA is said to target within, the sequence of a second dsRNA if the dsRNA cleaves the message anywhere within the mRNA that is complementary to the antisense strand of the second dsRNA. Such a dsRNA will generally have least 5, at least 10, at least 15, at least 18, or at least 20 contiguous nucleotides from one of the sequences provided in Table 1 and Table 2 coupled to additional nucleotide sequences taken from the region contiguous to the selected sequence in an mRNA encoding an Aha gene. For example, the 3'-most 15 nucleotides of the target sequence of AL-DP-7301 combined with the next 6 nucleotides from the target Aha1 gene produces a single strand agent of 21 nucleotides that is based on one of the sequences provided in Table 1 and Table 2.

Preferably, the second dsRNA is chosen from the group of dsRNAs having a certain activity in inhibiting the expression of an Aha gene in a suitable assay, such as the assays described herein. Consequently, in certain preferred embodiments, the second dsRNA is chosen from the group of AL-DP-7301, AL-DP-7308, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, AL-DP-7342, AL-DP-7303, AL-DP-7305, AL-DP-7307, AL-DP-7309, AL-DP-7316, and AL-DP-7337, AL-DP-7304, AL-DP-7312, AL-DP-733.9, AL-DP-7344, AL-DP-7306, AL-DP-7317, AL-DP-7346, AL-DP-7310, AL-DP-7323, AL-DP-7335, AL-DP-7338, AL-DP-7341, AL-DP-7302, AL-DP-7315, AL-DP-7328, AL-DP-7330, AL-DP-7336, AL-DP-7345, AL-DP-9250, AL-DP-9251, AL-DP-9252, AL-DP-9253, AL-DP-9254, AL-DP-9255, AL-DP-9256, AL-DP-9257, AL-DP-9258, AL-DP-9259, AL-DP-9260, AL-DP-9261, AL-DP-9262, AL-DP-9263, AL-DP-9264, AL-DP-9265, AL-DP-9266, AL-DP-9267, AL-DP-9268, AL-DP-9269, AL-DP-9270, AL-DP-9271, AL-DP-9272, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9284, AL-DP-9285, AL-DP-9286, AL-DP-9287, AL-DP-9288, and AL-DP-9289.

The dsRNA of the invention can contain one or more mismatches to the target sequence. In a preferred embodiment, the dsRNA of the invention contains no more than 3 mismatches, if the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity, and preferably from the 5'-end. For example, for a 23 nucleotide dsRNA strand which is complementary to a region of an Aha gene, the dsRNA generally does not contain any mismatch within the central 13 nucleotides. In another embodiment, the antisense strand of the dsRNA does not contain any mismatch in the region from positions 1, or 2, to positions 9, or 10, of the antisense strand (counting 5'-3'). The methods described within the invention, can be used to determine whether a dsRNA containing a mismatch to a target sequence is effective in inhibiting the expression of an Aha gene. Consideration of the efficacy of dsRNAs with mismatches in inhibiting expression of an Alia gene is important, especially if the particular region of complementarity in an Aha gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John. Wiley & Sons, Inc., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part, from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleotides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have, excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, hut are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleotides with heteroatom backbones, and in particular .$CH_2$.NH.$CH_2$., .$CH_2$.N($CH_3$).O.$CH_2$. [known as a methylene (methylimino) or MMI backbone], .$CH_2$.O.N($CH_3$).$CH_2$., .$CH_2$.N($CH_3$).N($CH_3$).$CH_2$. and .N($CH_3$).$CH_2$.$CH_2$. [wherein the native phosphodiester backbone is represented as .O.P.O.$CH_2$.] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl: O-, S-, or N-alkenyl; O-, S or N-alkynyl; or O-alkyl-O-alkyl, wherein the alkyl, alkenyl and alkynyl may be substituted or unsubstituted to $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_2$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O.$CH_2CH_2OCH_3$, also known as 2'-O-(2-methoxyethyl) or 2'-MOB) (Martin et al., Helv. Chim. Acta, 1995, 78, 486-504) i.e., an alkoxy-alkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O.$CH_2$.O.$CH_2$.N($CH_2$)$_2$, also described in examples hereinbelow.

Other preferred modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981, 957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687, 808, those disclosed in The Concise Encyclopedia Of Polymer Science And Engineering, pages 858-859, Kroschwitz, J. L., ed. John Wiley & Sons. 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown, to increase nucleic acid duplex stability by 0.6-1.2.degree, C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs of the invention involves chemically linking to the dsRNA one or more moieties or conjugates which enhance the activity, cellular distribution or cellular uptake of the dsRNA. Such moieties. Include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let, 1994 4 1053-1060), a thioether, e.g., beryl-S-tritylthiol (Manoharan et al., Ann. N.Y. Acad. Sci., 1992, 660, 306-309; Manoharan et al., Biorg. Med. Chem. Let, 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochemie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, hut are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603:5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873:5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions is a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region, wherein the dsRNA is modified so as to confer upon the dsRNA increased resistance to nuclease degradation. Increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86: 6553), cholic acid (Manoharan et al., Bioorg. Med. Chem. Lett., 1994, 4:1053), a thioether, e.g., hexyl-S-tritylthiol (Manoharan et al., Ann. N.Y., Acad. Sci., 1992, 660:306; Manoharan et al., Bioorg, Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651: Shea et al., Nucl. Acids Res., 1990, 18:3777), a polyamine or a polyethylene glycol chain (Manoharan et al. Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded RNAi Agents

The dsRNA of the invention can also be expressed from recombinant viral vectors intracellularly in vivo. The recombinant viral vectors of the invention comprise sequences encoding the dsRNA of the invention and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the dsRNA in a particular tissue or in a particular intracellular environment. The use of recombinant viral vectors to deliver dsRNA of the invention to cells in vivo is discussed in more detail below.

dsRNA of the invention can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2:301-310; Eglitis M A (1988), Biotechniques 6:608-614; Miller A D (1990), Hum Gene Therap. 1:5-14; Anderson W P (1998), Nature 392:25-30; and Rubinson D A et al., Nat. Genet. 33:401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20:1006-1010.

Suitable AAV vectors for expressing the dsRNA of the invention, methods for constructing the recombinant AV vector, and methods for delivering the vectors into target cells are described in Samulski R et al. (1987), J. Virol. 61:3096-3101; Fisher K J et al., (1996), J. Virol, 70:520-532; Samulski R et al. (1989), J. Virol. 63; 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of an Aha gene, such as pathological processes mediated by Aha1 expression. Such pharmaceutical compositions are formulated based on the mode of delivery. One example is compositions that are formulated for systemic administration via parenteral delivery.

The pharmaceutical compositions of the invention are administered in dosages sufficient to inhibit expression, of an Aha gene. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of an Aha gene.

In general, a suitable dose of dsRNA will be in the range of 0.01 microgram to 5.0 milligrams per kilogram body weight of the recipient per day, generally in the range of 1 microgram to 1 mg per kilogram body weight per day. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g. using a conventional sustained release formulation which provides sustained release of the dsRNA over a several day period. Sustained release formulations are well known, in the art and are particularly useful for vaginal delivery of agents, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on fee basis of in vivo testing using an appropriate animal model, as described elsewhere herein.

Advances in mouse genetics have generated a number of mouse models for the study of various human diseases, such as pathological processes mediated by Aha expression. Such models are used for in vivo testing of dsRNA, as well as for determining a therapeutically effective dose.

The present invention also includes pharmaceutical compositions and formulations which include the dsRNA compounds of the invention. The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical, formulations include those in which the dsRNAs of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl ethanolamine=DOPE, dimyristoylphosphatidyl choline=DMPC, distearolyphosphatidyl choline) negative (e.g. dimyristoylphosphatidyl glycerol=DMPG) and cationic (e.g. dioleoyltetramethylaminopropyl=DOTAP and dioleoylphosphatidyl ethanolamine=DOTMA). DsRNAs of the invention may be encapsulated within liposomes or may form, complexes thereto, in particular to cationic liposomes. Alternatively, dsRNAs may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which dsRNAs of the invention are administered in conjunction with one or more penetration enhancers, surfactants, and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxyeholic acid, taurocholic acid, taurodeoxycholic acid, sodium tauro-24,25-dihydro-4-fusidate and sodium glycodihydrofusidate. Preferred, fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. DsRNAs of the invention may be delivered orally, in granular form including sprayed dried particles, or complexed to form micro or nanoparticles. DsRNA complexing agents include poly-amino acids; polyimines; polyacrylates; polyalkylaerylates, polyoxethanes, polyalkylcyanoacrylates; canonized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly (methylcyanoacrylate), poly(ethylcyanoacrylate), poly(butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly (D,L-lactic acid), poly(DL-lactic-co-glycolic acid (PLGA), alginate, and polyethyleneglycol (PEG). Oral formulations for dsRNAs and their preparation are described in detail in U.S. application Ser. No. 08/886,829 (filed Jul., 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carriers) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p, 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, inc., New York, N. Y., volume 1, p, 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fate, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, In Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth, of microbes, these formulations often incorporate preservatives. Commonly used preservatives. Included in emulsion, formulations include methyl, paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have, been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system, of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to live components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p, 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed, spontaneously.

Surfactants used in the preparation of microemulsions include, but are not limited to, ionic surfactants, non-ionic surfactants, Brij 96, polyoxyethylene oleyl ethers, polyglycerol tatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate ($SO_{750}$), decaglycerol decaoleate (DAO750), alone or in combination with cosurfactants. The (cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known, in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_9$-$C_{10}$ glycerides, vegetable oils and silicone oil.

Microemulsions are particularly of interest from the standpoint of drug solubilization and the enhanced absorption of drugs, lipid based microemulsions (both o/w and w/o) have been proposed to enhance the oral bioavailability of drugs, including peptides (Constantinides et al., Pharmaceutical Research, 1994, 11, 1385-1390: Ritschel, Meth. Find. Exp. Clin. Pharmacol, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al. Pharmaceutical Research, 1994, 11, 1385; Ho et al., J. Pharm. Sci, 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids within the gastrointestinal tract, vagina, buccal cavity and other areas of administration.

Microemulsions of the present invention may also contain additional components and additives such as sorbitan monostearate (Grill 3), Labrasol and penetration enhancers to improve the properties of the formulation and to enhance the absorption of the dsRNAs and nucleic acids of the present invention. Penetration enhancers used in the microemulsions of the present invention may be classified as belonging to one of five broad categories surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest, because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: liposomes obtained from natural phospholipids are biocompatible and biodegradable; liposomes can incorporate a wide range of water and lipid soluble drugs; liposomes can protect encapsulated drugs is their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations is the preparation of liposome formulations are the lipid surface charge, vesicle size and the aqueous volume of the liposomes.

Liposomes are useful for the transfer and delivery of active Ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents info the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than, complex, formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidyl choline (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean. PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Werner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-Ionic surfactant and cholesterol, Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (He et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_m1$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42: Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_m1$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_m1$ or a galactocerebroside sulfate ester. U.S. Pat. No. 5,543,152 (Webb et al.) discloses liposomes comprising sphingomyelin. Liposomes comprising 1,2-sn-dimyristosylphosphat-idylcholine are disclosed in WO 97/13499 (Lim et al).

Many liposomes comprising lipids derivatized with one or more hydrophilic polymers, and methods of preparation thereof, are known in the art. Sunamoto et al., (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett, 1990, 268, 235) described experiments demonstrating that Liposomes comprising phosphatidylethanolamine (PE) derivatized with PEG or PEG stearate have significant increases in blood circulation half-lives. Blume et al. (Biochimica et Biophysics Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent. No. EP 0 445 131 B1 and WO 90704384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556, 948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes, U.S. Pat. No. 5,264,221 to Tagawa et al. discloses protein-bonded liposomes and asserts that, the contents of such liposomes may include dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly dsRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer, in addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al. Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced, in addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43 (Takahashi et al., J. Pharm. Pharmacol, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_1$-$C_{10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drag Carrier Systems, 1991, p. 92; Muranishi, Critical Reviews in Therapeutic Drag Carrier Systems, 1990, 7, 1-33; El Hariri et al., J. Pharm. Pharmacol, 1992, 44, 651-654).

Bile salts: The physiological role of bile includes the facilitation of dispersion and absorption of lipids and fat-soluble, vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium chelate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drag Carrier Systems, 1991, page 92; Swinyard, Chapter 39 In: Remington's Pharmaceutical Sciences, 18th Ed., Gennaro, ed. Mack Publishing Co., Easton, Pa., 1990, pages 782-783; Muranishi, Critical Reviews in Therapeutic Drug Carrier Systems, 1990, 7, 1-33: Yamamoto et al., J. Pharm. Exp. Ther., 1992, 263, 25; Yamashita et al., J. Pharm. Sci., 1990, 79, 579-583).

Chelating Agents: Chelating agents, as used in connection with the present, invention, can be defined as compounds feat remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1996, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al., U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes suck as limonene and menthone.

Carriers

Certain compositions of the present invention also incorporate carrier compounds in the formulation. As used herein, "carrier compound" or "carrier" can refer to a nucleic acid, or analog thereof, which is inert, (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4 isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Pharmaceutical Compositions for the Delivery to the Respiratory Tract

Another aspect of the invention provides for the delivery of IRNA agents to the respiratory tract, particularly for the treatment of cystic fibrosis. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung. The deep lung, or alveoli, are the primary target of inhaled therapeutic aerosols for systemic delivery of iRNA agents.

Pulmonary delivery compositions can be delivered by inhalation, by the patient of a dispersion so that the composition, preferably the iRNA agent, within the dispersion can reach the lung where it can, for example, be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations; administration by inhalation may be oral and/or nasal. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

Examples of pharmaceutical devices for aerosol delivery include metered dose inhalers (MDIs), dry powder inhalers (DPIs), and air-jet nebulizers. Exemplary delivery systems by inhalation which can be readily adapted for delivery of the subject iRNA agents are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the iRNA agents are described in U.S. Pat. Nos. 6,294,153; 6,344,194; 6,071,497, and PCT applications WO02/066078; WO02/053190; WO01/60420; WO00/66206. Further, methods for delivering iRNA agents can be adapted from those used in delivering other oligonucleotides (e.g., an antisense oligonucleotide) by inhalation, such as described in Templin et al., Antisense Nucleic Acid Drug Dev, 2000, 10:359-68; Sandrasagra et al. Expert Opin Biol Ther, 2001, 1:979-83; Sandrasagra et al., Antisense Nucleic Acid Drag Dev, 2002, 12:177-81.

The delivery of the inventive agents may also involve the administration of so called "pro-drugs", i.e. formulations or chemical modifications of a therapeutic substance that require some form of processing or transport by systems innate to the subject organism to release the therapeutic substance, preferably at the site where its action is desired; this latter embodiment may be used in conjunction with delivery of the respiratory tract, but also together with other embodiments of the present invention. For example, the human lungs can remove or rapidly degrade hydrolytically cleavable deposited aerosols over periods ranging from minutes to hours. In the upper airways, ciliated epithelia contribute to the "mucociliary escalator" by which particles are swept from the airways toward, the mouth. Pavia, D., "Lung Mucociliary Clearance," in Aerosols and the Lung: Clinical and Experimental Aspects, Clarke, S. W. and Pavia, D. Eds., Butterworths, London, 1984. In the deep lungs, alveolar macrophages are capable of phagocytosing particles soon after their deposition. Warheit et al. Microscopy Res. Tech., 26: 412-422 (1993); and Brain, J, D., "Physiology and Pathophysiology of Pulmonary Macrophages," in The Reticuloendothelial System, S. M. Reichard and J. Filkins, Eds., Plenum, New. York., pp. 315-327, 1985.

In preferred embodiments, particularly where systemic dosing with the iRNA agent is desired, the aerosoled iRNA agents are formulated as microparticles, Microparticles having a diameter of between 0.5 and ten microns can penetrate the lungs, passing through most of the natural barriers. A diameter of less than ten microns is required to bypass the throat; a diameter of 0.5 microns or greater is required to avoid being exhaled.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage tonus of the compositions of the present invention, such as dyes, flavoring agents, preservatives, antioxidants, opacifiers, thickening agents and stabilizers. However, such materials, when, added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxylmethylcellulose, sorbitol and/or dextran. The suspension may also contain stabilizers.

Certain embodiments of the invention provide pharmaceutical compositions containing (a) one or more ds RNA agents and (b) one or more other chemotherapeutic agents which function by a non-RNA interference mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Railway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-dsRNA chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of pathological processes mediated by Aha expression. In any event, the administering physician can adjust the amount and timing of dsRNA administration on the basis of results observed using standard measures of efficacy known in the art or described herein.

Methods for Treating Diseases Caused by Expression of an Aha Gene

The invention relates in particular to the use of a dsRNA or a pharmaceutical composition prepared therefrom for the treatment of Cystic Fibrosis. Owing to the inhibitory effect on Aha1 expression, an dsRNA according to the invention or a pharmaceutical composition prepared therefrom can enhance the quality of life of Cystic Fibrosis patients.

Furthermore, the invention relates to the use of a dsRNA or a pharmaceutical composition of the invention aimed at the treatment of cancer, e.g. for inhibiting tumor growth and tumor metastasis. For example, the dsRNA or a pharmaceutical composition prepared therefrom may be used for the treatment of solid tumors, like breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma and for the treatment of skin cancer, like melanoma, for the treatment of lymphomas and blood cancer. The invention further relates to the use of an dsRNA according to the invention or a pharmaceutical composition prepared therefrom, for inhibiting Aha1 expression and/or for inhibiting accumulation of ascites fluid and pleural effusion in different types of cancer, e.g., breast cancer, lung cancer, head cancer, neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, melanoma, lymphomas and blood cancer. Owing to the inhibitory effect on Aha1 expression, an dsRNA according to the invention or a pharmaceutical composition prepared therefrom can enhance the quality of life of cancer patients.

The invention furthermore relates to the use of an dsRNA or a pharmaceutical composition thereof, e.g., for treating Cystic Fibrosis or cancer or for preventing tumor metastasis, in combination with other pharmaceuticals and/or other therapeutic methods, e.g., with known pharmaceuticals and/or known therapeutic methods, such as, for example, those which are currently employed, for treating Cystic Fibrosis or cancer and/or for preventing tumor metastasis. Where the pharmaceutical composition aims for the treatment of Cystic fibrosis, preference is given to a combination with daily chest physiotherapy, orally applied pancreatic enzymes, daily oral or inhaled antibiotics to counter lung infection, inhaled anti-asthma therapy, corticosteroid tablets, dietary vitamin supplements, especially A and D, inhalation of Pulmozyme™, medicines to relieve constipation or to improve the activity of the enzyme supplements, insulin for CF-related diabetes, medication for CF-associated Liver disease, and oxygen to help with breathing.

Where the pharmaceutical composition aims for the treatment of cancer and/or for preventing tumor metastasis, preference is given to a combination with radiation therapy and chemotherapeutic agents, such as cisplatin, cyclophosphamide, 5-fluorouracil, adriamycin, daunorubicin or tamoxifen.

The invention can also be practiced by including with a specific RNAi agent another anti-cancer chemotherapeutic agent, such as any conventional chemotherapeutic agent. The combination of a specific binding agent with such other agents can potentiate the chemotherapeutic protocol Numerous chemotherapeutic protocols will present themselves in the mind of the skilled practitioner as being capable of incorporation into the method of the invention. Any chemotherapeutic agent can be used, including alkylating agents, antimetabolites., hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the ease of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the Invention can be employed with such conventional regimens with the benefit of reducing side effects and enhancing efficacy.

Methods for Inhibiting Expression of an Aha Gene

In yet another aspect, the invention provides a method for inhibiting the expression of an Aba gene in a mammal. The method comprises administering a composition of the invention to the mammal such that expression of the target Aha gene, e.g. Aha1, is silenced. Because of their high specificity, the dsRNAs of the invention specifically target RNAs (primary or processed) of the target Aha gene. Compositions and methods for inhibiting the expression of these Aha genes using dsRNAs can be performed as described elsewhere herein.

In one embodiment, the method comprises administering a composition comprising a dsRNA, wherein the dsRNA comprises a nucleotide sequence which is complementary to at least apart of an RNA transcript of an Aha gene, e.g. Aha1, of the mammal to be treated. When the organism to be treated is a mammal such as a human, the composition may be administered by any means known in the art including, but not limited to oral or parenteral routes, including intravenous, intramuscular, subcutaneous, transdermal, airway (aerosol), nasal rectal, vaginal and topical (including buccal and sublingual) administration. In preferred embodiments, the compositions are administered by intravenous infusion or injection.

Unless otherwise defined, all technical and scientific terms used, herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are Incorporated by reference in their entirety. In ease of conflict, the present specification, including definitions, will control. In addition, the materials, methods, and examples are illustrative only and not intended to be limiting.

EXAMPLES

Gene Walking of an Aha Gene siRNA design was carried out to identify siRNAs targeting Aha1. The mRNA sequences of *Homo sapiens* (NM_012111.1), *mus musculus* (NM_46036.1) and pan troglodytes (XM_510094.1) Aha 1 were examined by computer analysis to identify homologous sequences of 19 or 21 nucleotides that yield RNAi agents cross-reactive between these three species. Of those identified, 48 such sequences were selected for minimal off-target interactions in rats (at least 3 mismatches, to any other gene in the rat genome, or at least two mismatches to any other gene in the rat genome, wherein one of said at least two mismatches is located in a position complementary to position 9 or 10 of the antisense strand of the corresponding RNAi agent, counting 5' to 3') and the corresponding dsRNAs synthesized for screening (AL-DP-7301-AL-DP-7346, see Table 1), AL-DP-7561, AL-DP-7562, AL-DP-7563 and AL-DP-7564 which are additionally cross-reactive to *mus musculus* (NM_172391.3) and *rattus norvegicus* (XM_223680.3) Aha 2, were also synthesized and screened. In addition, a further 40 sequences were selected for minimal predicted off-target interactions in humans (at least 3 mismatches to any other gene in the human genome, or at least two mismatches to any other gene in the human genome, wherein one of said at least two mismatches is located in a position complementary to position 9 or 10 of the antisense strand of the corresponding RNAi agent, counting 5' to 3') and the corresponding dsRNAs synthesized for screening (AL-DP-9250-AL-DP-9289, see Table 2). 17 sequences were identified as belonging to both sets (AL-DP-7301, AL-DP-7304, AL-DP-7305, AL-DP-7307, AL-DP-7310, AL-DP-7312, AL-DP-7315, AL-DP-7316, AL-DP-7317, AL-DP-7323, AL-DP-7324, AL-DP-7332, AL-DP-7336, AL-DP-7337, AL-DP-7338, AL-DP-7342, and AL-DP-7344.

dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the Iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection mid purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

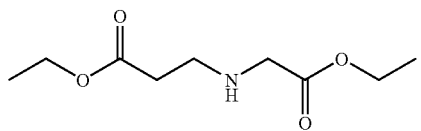

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

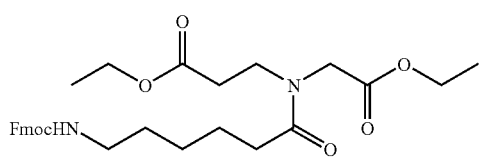

Fmoc-6-ammo-hexanoic acid (9.12 g. 25.83 mmol) was dissolved in dichloromethane (50 mL) and cooled with ice. Diisopropylcarbodiimide (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl area. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

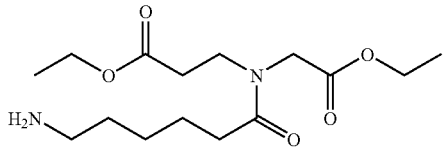

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethyl amine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (103 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

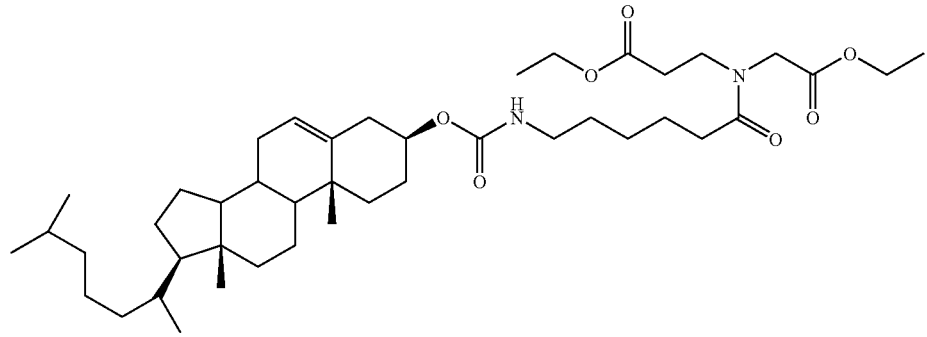

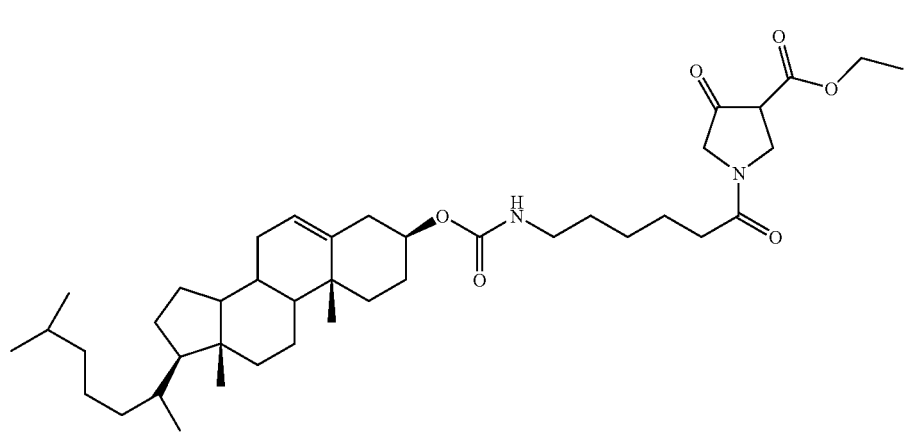

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water. The resultant mixture was extracted twice with 100 mL of dichloromethane each and the combined organic extracts were washed twice with 10 mL of phosphate buffer each, dried, and evaporated to dryness. The residue was dissolved in 60 ml, of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethyl acetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

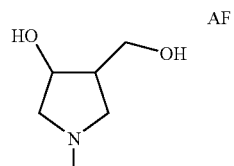

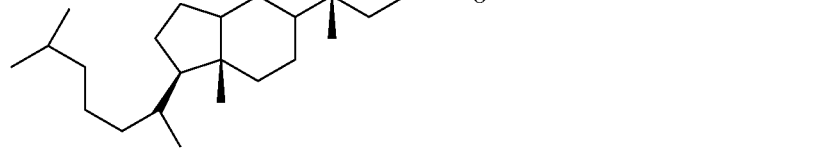

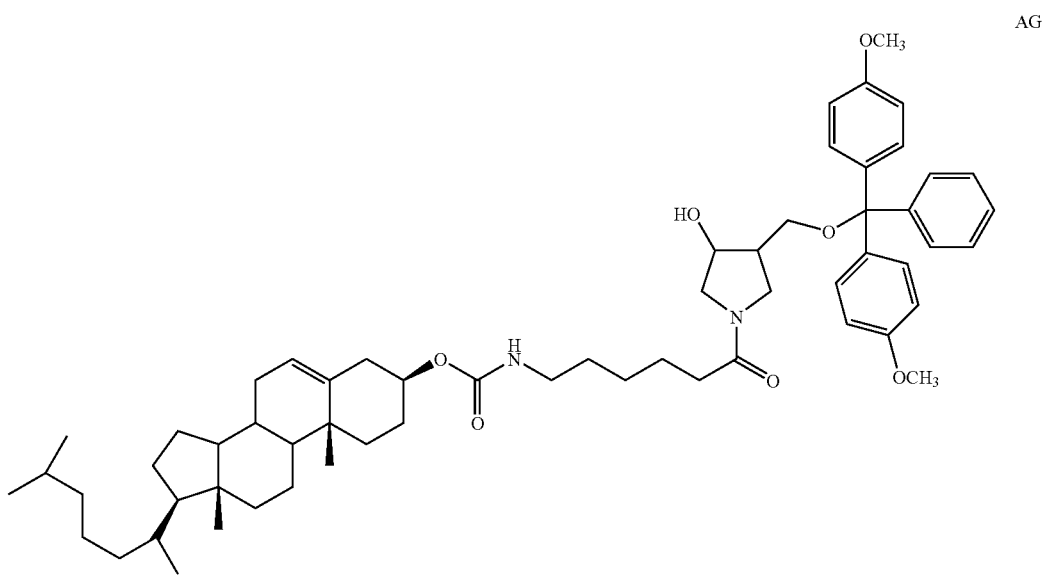

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room, temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic add mono-(4-[bis(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH Compound AG (1.0 g, 1.05 mmol) was mixed with succinic anhydride (0.150 g, 1.5 mmol) and DMAP (0.073 g, 0.6 mmol) and dried, in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step;

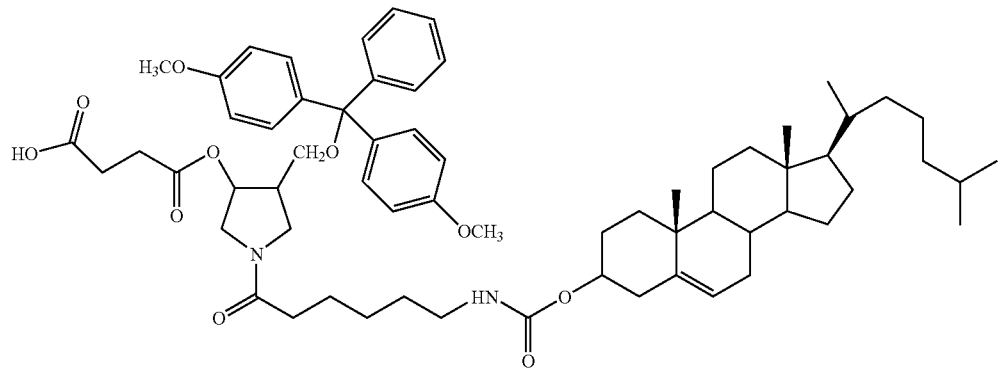

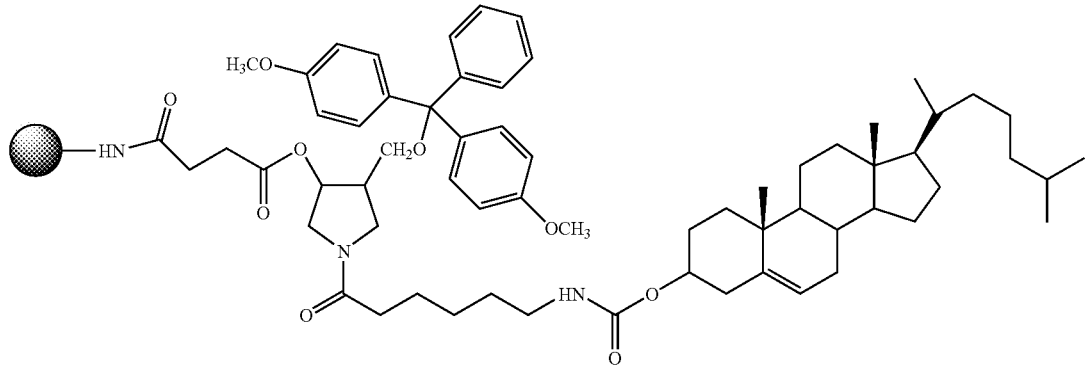

Cholesterol Derivatised CPG AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphospine (0.064 g, 0.242 mmol) in acetonitrile (0.6 ml) was added. The reaction mixture turned bright orange in color. The solution was agitated briefly using a wrist-action-shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except, that, for the cholesteryl derivative, the oxidation step was performed using the Beaucage reagent in order to introduce a phosphorothioate linkage at the 5'-end of the nucleic acid oligomer.

Nucleic acid sequences are represented below using standard nomenclature, and specifically the abbreviations of Table 2.

TABLE 3

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucelotide(s) |
| --- | --- |
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| Am | 2'-O-methyladenosine-5'-phosphate |
| Cm | 2'-O-methylcytidine-5'-phosphate |
| Gm | 2'-O-methylguanosine-5'-phosphate |
| Tm | 2'-O-methyl-thymidine-5'-phosphate |
| Um | 2'-O-methyluridine-5'-phosphate |
| Af | 2'-fluoro-2'-deoxy-adenosine-5'-phosphate |
| Cf | 2'-fluoro-2'-deoxy-cytidine-5'-phosphate |
| Gf | 2'-fluoro-2'-deoxy-guanosine-5'-phosphate |
| Tf | 2'-fluoro-2'-deoxy-thymidine-5'-phosphate |
| Uf | 2'-fluoro-2-deoxy-uridine-5'-phosphate |
| <u>A</u>, <u>C</u>, <u>G</u>, <u>T</u>, <u>U</u>, <u>a</u>, <u>c</u>, <u>g</u>, <u>t</u>, <u>u</u> | underlined: nucleoside-5'-phosphorothioate |
| <u>am</u>, <u>cm</u>, <u>gm</u>, <u>tm</u>, <u>um</u> | underlined: 2-O-methyl-nucleoside-5'-phosphorothioate |

[a] capital letters represent 2'-deoxyribonucleotides (DNA), lower case letters represent ribonucleotides (RNA)

dsRNA Expression Vectors

In another aspect of the invention, Aha1 specific dsRNA molecules that modulate Aha1 gene expression activity are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication. No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression, vectors are generally DNA plasmids or viral vectors dsRNA expressing viral vectors can be constructed based on, but not limited to, adeno-associated virus (for a review, see Muzyezka, et al., Curr. Topics Micro. Immunol. (1992) 158:97-129)); adenovirus, (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into marry different cell types, including epithelial cells, in vitro and/or in vivo (see, e.g., Eglitis, et al., Science (1985) 230:1395-1398; Danes and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Hubet et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10: Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation, by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single Aha1 gene or multiple Aha1 genes over a period, of a week or more are also contemplated by the invention. Successful introduction of the vectors of the invention, into host cells can be monitored using various known methods. For example, transient transfection can be signaled with a reporter, such as a fluorescent marker, such as Green Fluorescent Protein (GFP). Stable transfection. of ex vivo cells can be ensured using markers that provide the transfected cell with resistance to specific environmental, factors (e.g., antibiotics and drags), such as hygromycin B resistance.

The Aha1 specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Aha1 siRNA In Vitro Screening

Single Dose Screen in HeLa and MLE 12 Cells

HeLa cells were obtained from American Type Culture Collection (Rockville, Md., cat. No. HB-8065) and cultured in Ham's F12 (Biochrom AG, Berlin, Germany cat. No. FG0815) supplemented to contain 10% fetal calf serum (FCS) (Biochrom AG, Berlin, Germany, cat. No. S0115), Penicillin 100 U/ml, Streptomycin 100 µg/ml (Biochrom AG, Berlin, Germany, cat. No. A2213) at 37° C. in an atmosphere with 5% $CO_2$ in a humidified incubator (Heraeus HERAcell, Kendro Laboratory Products, Langenselbold, Germany).

MLE 12 cells were obtained from American Type Culture Collection (Rockville, Md., cat. No. CRL-2110) and cultured in HITES Medium (1:1 mix Dulbecco's MEM (Biochrom AG, Berlin, Germany, cat. No: F0435)+Ham's F12 (Biochrom AG, Berlin, Germany, cat No: FG0815)) supplemented to contain 2% fetal calf serum (FCS) (Biochrom AG, Berlin, Germany, cat. No. S0115), Penicillin 100 U/ml, Streptomycin 100 µg/ml (Biochrom AG, Berlin, Germany, cat. No. A2213), 4 mM L-Glutamin (Biochrom AG, Berlin, Germany, cat. No: K0282), 1× Insulin/Transferrin/Na-Selenit (Gibco: 51500-056), 10 nM Hydrocortisone (Sigma Munich, Germany, cat. No: H6909), 10 nM β-Estradiol (Sigma Munich, Germany, cat No: E2257), and 10 mM; HEPES (USB Europe GmBH, Staufen, Germany cat No.: 16926) at 37° C. in an atmosphere with 5% $CO_2$ in a humidified incubator (Heraeus HERAcell, Kendro Laboratory Products, Langenselbold, Germany).

Transfection and mRNA Quantification

For transfection with siRNA, HeLa and MLE12 cells were seeded at a density of $2.0 \times 10^4$ cells/well in 96-well plates and transfected directly. Transfection of siRNA (30 nM) was carried out with lipofectamine 2000 (Invitrogen GmbH, Karlsruhe, Germany, cat. No. 11068-019) as described by the manufacturer. 24 hours after transfection cells were lysed and Aha1 mRNA levels were quantified with the Quantigene Explore Kit (Genosprectra, Dumbarton Circle Fremont, USA, eat. No. QG-000-02) according to the manufacturer's protocol, Aha1 mRNA levels were normalized to GAPDH mRNA. Readings were obtained in quadruplicates for each siRNA. siRNA duplexes unrelated to Aha1 gene were used as control. The activity of a given Aha1 specific siRNA duplex was expressed as percent Aha1 mRNA concentration in treated cells relative to Aha1 mRNA concentration in cells treated with the control siRNA duplex.

TABLE 4

Probe sequences used with Quantigene Explore Kit (Genospectra) in quantification of *Homo Sapiens* (hs) Aha1

| FPL Name | Function | Sequence | SEQ ID NO: |
|---|---|---|---|
| hsAha1 001 | CE | GATGTAAATTCCCATTGCTTCTCTTTTTCTCTTGGAAAGAAAGT | 185 |
| hsAha1 002 | CE | TGAACTCTGTTTTGAGGGTGCTTTTTTCTCTTGGAAAGAAAGT | 186 |
| hsAha1 003 | CE | GGGTCTACTGACTCTCCATTCATTGTTTTCTCTTGGAAAGAAAGT | 187 |
| hsAha1 004 | CE | CCTTGCGCTCCTCAGTTTTCTTTTTCTCTTGGAAAGAAAGT | 188 |
| hsAha1 005 | CE | GGTTTTTGAAGGAGCAGGCTTAGTTTTTCTCTTGGAAAGAAAGT | 189 |
| hsAha1 006 | LE | ACGCTGTTTTCATCAGACAAATTTTTTTAGGCATAGGACCCGTGTCT | 190 |
| hsAha1 007 | LE | GCTCACACTAATCTCCACTTCATCCTTTTTAGGCATAGGACCCGTGTCT | 191 |

TABLE 4-continued

Probe sequences used with Quantigene Explore Kit (Genospectra) in quantification of *Homo Sapiens* (hs) Aha1

| FPL Name | Function | Sequence | SEQ ID NO: |
|---|---|---|---|
| hsAha1 008 | LE | TCATTAAGGCCACGAGATTTGTTTTTTAGGCATAGGACCCGTGTCT | 192 |
| hsAha1 009 | LE | TAGGTAAGATCATGCCCTGGGTTTTTAGGCATAGGACCCGTGTCT | 193 |
| hsAha1 010 | LE | ACTCCAACAGGTCTGGCCTGTTTTTAGGCATAGGACCCGTGTCT | 194 |
| hsAha1 011 | BL | GTCAGGCTCATCTTTGGCAAG | 195 |
| hsAha1 012 | BL | TAGAAGTTTCACCCCTTCTTCCT | 196 |
| hsAha1 013 | BL | AGTGCTGGCTGCCCCACT | 197 |

TABLE 5

Probe sequences used with Quantigene Explore Kit (Genospectra) in quantification of *Mus musculus* (mm) Aha1

| FPL Name | Function | Sequence | SEQ ID NO: |
|---|---|---|---|
| mmAhsa 1001 | CE | CTCGAACGGCCAGGAACATTTTTCTCTTGGAAAGAAAGT | 198 |
| mmAhsa 1002 | CE | GCACTTGCCCTCTTCATTTTCTATTTTTCTCTTGGAAAGAAAGT | 199 |
| mmAhsa 1003 | CE | TTGATGGATGCCTCCCCATTTTTTCTCTTGGAAAGAAAGT | 200 |
| mmAhsa 1004 | CE | AACTCTGTCTTGAGGGTGCTGATTTTTTCTCTTGGAAAGAAAGT | 201 |
| mmAhsa 1005 | CE | TTTGGCCTGGCTTTTTGAATTTTTCTCTTGGAAAGAAAGT | 202 |
| mmAhsa 1006 | LE | CAAGCTTGTTCACTTCGGTCACCTCTTTTTAGGCATAGGACCCGTGTCT | 203 |
| mmAhsa 1007 | LE | CCTGACTTAGAGGTACCTGTCCAGTTTTTTAGGCATAGGACCCGTGTCT | 204 |
| mmAhsa 1008 | LE | GATTTCCACATGTCCTTTGTACTGCACTTTTTAGGCATAGGACCCGTGTCT | 205 |
| mmAhsa 1009 | LE | ATTTTCATCAGACAAATTGGGTTTTTAGGCATAGGACCCGTGTCT | 206 |
| mmAhsa 1010 | LE | TAATCTCCACTTCATCCACGCTTTTTAGGCATAGGACCCGTGTCT | 207 |
| mmAhsa 1011 | LE | TTTCACCCCGTCTTCCTTCATTTTTAGGCATAGGACCCGTGTCT | 208 |
| mmAhsa 1012 | LE | ACTGTGGGCAAGATCATGCCCTGAGTATTTTAGGCATAGGACCCGTGTCT | 209 |
| mmAhsa 1013 | BL | AAGATAAGTTTGCCTTTCCTGTTG | 210 |
| mmAhsa 1014 | BL | CAGTTTGATGGTCCACTCATAGAAG | 211 |
| mmAhsa 1015 | BL | CATCTTTGGCAAGGCTCACAC | 212 |
| mmAhsa 1016 | BL | TTAAGGCCACGAGATTTGTGTCAGGCT | 213 |
| mmAhsa 1017 | BL | GTAAATTCCCACTGCTTCTCTCAGAAG | 214 |
| mmAhsa 1018 | BL | CACTGGATCTACTGACTCTCCATTC | 215 |
| mmAhsa 1019 | BL | CTCAGTCTTTAGTGCTGGCTGGCC | 216 |
| mmAhsa 1020 | BL | GGAGCAGACTTAGCCTTGCAAGT | 217 |

Dose-Response Curves in HeLa Cells

Transfection and mRNA quantification: For transfection with siRNA, HeLa cells were seeded at a density of $2.0 \times 10^4$ cells/well in 96-well plates and transfected directly. Transfection of siRNA was carried out with lipofectamine 2000 (Invitrogen GmbH, Karlsruhe, Germany, cat. No. 11668-019) as described by the manufacturer. siRNAs were concentrated from 30 nM in 3 fold dilutions to 14 pM, 24 hours after transfection HeLa cells were lysed and Aha1 mRNA levels were quantified with the Quantigene Explore Kit (Genosprectra, Dumbarton Circle Fremont, USA, cat No. QG000-02) according to the protocol. Aha1 mRNA levels were normalized to GAP-DH mRNA. For each siRNA four individual datapoints were collected, siRNA duplexes unrelated to Aha1 gene were used, as control. The activity of a given Aha1 specific siRNA duplex was expressed as percent Aha1 mRNA concentration in treated cells relative to Aha1 mRNA concentration in cells treated with the control siRNA duplex. XL-fit was, used to calculate $IC_{50}$ values.

Table 6 provides values for inhibition of Aha1 expression using various dsRNA molecules of the invention.

TABLE 6

Residual Aha1 mRNA in % of control in HeLa and MLE12 cells treated with 30 nM solutions of various RNAi agents specific for Aha1, and $IC_{50}$ for selected RNAi agents determined in HeLa cells

| Duplex identifier | HeLa cells, residual mRNA [%] | $IC_{50}$ in HeLa cells [nM] | MLE12 cells, residual mRNA [%] |
|---|---|---|---|
| AL-DP-7299 | 19 ± 3 | | 105 ± 17 |
| AL-DP-7300 | 7 ± 2 | | 94 ± 13 |
| AL-DP-7301 | 3 ± 1 | 0.035 | 14 ± 3 |
| AL-DP-7302 | 17 ± 5 | | 61 ± 16 |
| AL-DP-7303 | 5 ± 2 | | 23 ± 5 |
| AL-DP-7304 | 7 ± 3 | | 30 ± 7 |
| AL-DP-7305 | 6 ± 2 | | 26 ± 6 |
| AL-DP-7306 | 27 ± 8 | | 45 ± 11 |
| AL-DP-7307 | 16 ± 6 | 1.1 | 27 ± 8 |
| AL-DP-7308 | 13 ± 5 | 0.21 | 20 ± 7 |
| AL-DP-7309 | 10 ± 3 | 0.36 | 22 ± 8 |
| AL-DP-7310 | 51 ± 13 | | 59 ± 13 |
| AL-DP-7311 | 4 ± 3 | 0.07 | 16 ± 4 |
| AL-DP-7312 | 14 ± 3 | | 40 ± 8 |
| AL-DP-7313 | 63 ± 14 | | 80 ± 10 |
| AL-DP-7314 | 97 ± 21 | | 88 ± 10 |
| AL-DP-7315 | 76 ± 24 | | 77 ± 10 |
| AL-DP-7316 | 7 ± 2 | 0.34 | 23 ± 6 |
| AL-DP-7317 | 11 ± 3 | | 44 ± 12 |
| AL-DP-7318 | 4 ± 2 | 0.29 | 16 ± 3 |
| AL-DP-7319 | 38 ± 7 | | 73 ± 21 |
| AL-DP-7320 | 16 ± 4 | 0.07 | 15 ± 5 |
| AL-DP-7321 | 130 ± 36 | | 81 ± 16 |
| AL-DP-7322 | 4 ± 2 | 0.045 | 10 ± 3 |
| AL-DP-7323 | 24 ± 6 | | 55 ± 11 |
| AL-DP-7324 | 3 ± 2 | 0.089 | 12 ± 4 |
| AL-DP-7325 | 5 ± 2 | 0.3 | 12 ± 4 |
| AL-DP-7326 | 3 ± 1 | 0.27 | 19 ± 7 |
| AL-DP-7327 | 3 ± 1 | 0.08 | 13 ± 7 |
| AL-DP-7328 | 49 ± 14 | | 67 ± 10 |
| AL-DP-7329 | 6 ± 2 | 0.2 | 18 ± 5 |
| AL-DP-7330 | 64 ± 19 | | 78 ± 10 |
| AL-DP-7331 | 5 ± 2 | 0.55 | 13 ± 5 |
| AL-DP-7332 | 95 ± 20 | | 82 ± 15 |
| AL-DP-7333 | 2 ± 1 | 0.27 | 9 ± 3 |
| AL-DP-7334 | 94 ± 17 | | 83 ± 19 |
| AL-DP-7335 | 11 ± 5 | | 57 ± 11 |
| AL-DP-7336 | 22 ± 4 | | 63 ± 12 |
| AL-DP-7337 | 6 ± 2 | 0.29 | 20 ± 5 |
| AL-DP-7338 | 39 ± 6 | | 56 ± 10 |
| AL-DP-7339 | 10 ± 1 | | 35 ± 6 |
| AL-DP-7340 | 8 ± 2 | 0.61 | 19 ± 6 |
| AL-DP-7341 | 17 ± 4 | | 55 ± 16 |
| AL-DP-7342 | 6 ± 4 | 0.5 | 15 ± 3 |
| AL-DP-7343 | 26 ± 4 | | 103 ± 19 |
| AL-DP-7344 | 5 ± 2 | | 38 ± 11 |
| AL-DP-7345 | 53 ± 22 | | 63 ± 15 |
| AL-DP-7346 | 22 ± 4 | | 44 ± 11 |
| AL-DP-9250 | 4 ± 1 | | |
| AL-DP-9251 | 51 ± 9 | | |
| AL-DP-9252 | 19 ± 2 | | |
| AL-DP-9253 | 11 ± 1 | | |
| AL-DP-9254 | 7 ± 1 | | |
| AL-DP-9255 | 5 ± 0 | | |
| AL-DP-9256 | 5 ± 0 | | |
| AL-DP-9257 | 7 ± 0 | | |
| AL-DP-9258 | 9 ± 1 | | |
| AL-DP-9259 | 7 ± 1 | | |
| AL-DP-9260 | 15 ± 3 | | |
| AL-DP-9261 | 21 ± 2 | | |
| AL-DP-9262 | 24 ± 4 | | |
| AL-DP-9263 | 25 ± 6 | | |
| AL-DP-9264 | 7 ± 2 | | |
| AL-DP-9265 | 8 ± 1 | | |
| AL-DP-9266 | 11 ± 2 | | |
| AL-DP-9267 | 45 ± 4 | | |
| AL-DP-9268 | 9 ± 1 | | |
| AL-DP-9269 | 5 ± 1 | | |
| AL-DP-9270 | 6 ± 1 | | |
| AL-DP-9271 | 6 ± 2 | | |
| AL-DP-9272 | 26 ± 8 | | |
| AL-DP-9273 | 11 ± 1 | | |
| AL-DP-9274 | 7 ± 1 | | |
| AL-DP-9275 | 8 ± 1 | | |
| AL-DP-9276 | 4 ± 1 | | |
| AL-DP-9277 | 10 ± 1 | | |
| AL-DP-9278 | 2 ± 0 | | |
| AL-DP-9279 | 3 ± 0 | | |
| AL-DP-9280 | 12 ± 1 | | |
| AL-DP-9281 | 8 ± 2 | | |
| AL-DP-9282 | 3 ± 0 | | |
| AL-DP-9283 | 6 ± 1 | | |
| AL-DP-9284 | 39 ± 2 | | |
| AL-DP-9285 | 4 ± 1 | | |
| AL-DP-9286 | 61 ± 11 | | |
| AL-DP-9287 | 3 ± 1 | | |
| AL-DP-9288 | 27 ± 5 | | |
| AL-DP-9289 | 6 ± 1 | | |

In summary, AL-DP-7301, AL-DP-7303, AL-DP-7318, AL-DP-7320, AL-DP-7322, AL-DP-7324, AL-DP-7325, AL-DP-7326, AL-DP-7327, AL-DP-7329, AL-DP-7331, AL-DP-7333, AL-DP-7340, and AL-DP-7342 inhibited Aha1 expression by at least 80% in both HeLa and MLE12 cells, AL-DP-7303, AL-DP-7305, AL-DP-7307, AL-DP-7309, AL-DP-7316, and AL-DP-7337 inhibited Aha1 expression by at least 80% in HeLa cells and by at least 70% in MLE12 cells, AL-DP-7304, AL-DP-7312, AL-DP-7339, and AL-DP-7344 inhibited Aha1 expression by at least 80% in HeLa cells and by at least 60% in MLE12 cells, AL-DP-7306, AL-DP-7317, and AL-DP-7346 inhibited Aha1 expression by at least 70% in HeLa cells and by at least 50% in MLE 12 cells, AL-DP-7310, AL-DP-7323, AL-DP-7335, AL-DP-7338, and AL-DP-7341 inhibited Aha1 expression by at least 40% in both HeLa and MLE12 cells, and AL-DP-7302, AL-DP-7315, AL-DP-7328, AL-DP-7330, AL-DP-7336, and AL-DP-7345, inhibited Aha1 expression by at least 20% in both HeLa and MLE12 cells.

In addition, AL-DP-9250, AL-DP-9252, AL-DP-9253, AL-DP-9254, AL-DP-9255, AL-DP-9256, AL-DP-9257, AL-DP-9258, AL-DP-9259, AL-DP-9260, AL-DP-9264, AL-DP-9265, AL-DP-9266, AL-DP-9268, AL-DP-9269, AL-DP-9270, AL-DP-9271, AL-DP-9273, AL-DP-9274, AL-DP-9275, AL-DP-9276, AL-DP-9277, AL-DP-9279, AL-DP-9280, AL-DP-9281, AL-DP-9282, AL-DP-9283, AL-DP-9285, AL-DP-9287, and AL-DP-9289 inhibited Aha1 expression by at least 80% in HeLa cells, AL-DP-9261, AL-DP-9262, AL-DP-9263, AL-DP-9272, and AL-DP-9288 inhibited Aha1 expression by at least 70% in HeLa cells, AL-DP-9263 inhibited Aha1 expression by at least 60% in HeLa cells, AL-DP-9267 inhibited Aha1 expression by at least 50% in HeLa cells, AL-DP-9251 inhibited Aha1 expression by at least 40% in HeLa cells, and AL-DP-9286 inhibited Aha1 expression by at least 3.0% in HeLa cells.

We claim:

1. A double-stranded ribonucleic acid (dsRNA) for inhibiting the expression of a human Aha gene, wherein the dsRNA consists of SEQ ID NO:51 and SEQ ID NO:52.

2. The dsRNA of claim 1, wherein said Aha gene is an Aha1 gene.

3. The dsRNA of claim 1, wherein, upon contact with a cell expressing said Aha gene, the dsRNA inhibits mRNA expression of said Aha gene in said cell by at least 20% compared to a control siRNA duplex unrelated to said Aha gene.

4. The dsRNA of claim 3, wherein said at least 20% inhibition of mRNA expression of said Aha gene is effected in HeLa and/or MLE12 cells.

5. The dsRNA of claim 1, wherein said dsRNA, upon contact with a cell expressing said Aha, inhibits mRNA expression of said Aha gene by at least 25% compared to a control siRNA duplex unrelated to said Aha gene.

6. The dsRNA of claim 1, wherein said dsRNA, upon contact with a cell expressing said Aha, inhibits mRNA expression of said Aha gene by at least 40% compared to a control siRNA duplex unrelated to said Aha gene.

7. A cell comprising the dsRNA of claim 1.

8. A vector for inhibiting the expression of an Aha gene in a cell, said vector encoding the dsRNA of claim 1.

9. A cell comprising the vector of claim 8.

10. A pharmaceutical composition for inhibiting the expression of an Aha gene, comprising the dsRNA of claim 1 and a pharmaceutically acceptable carrier.

11. The pharmaceutical composition of claim 10, wherein said Aha gene is an Aha1 gene.

12. The pharmaceutical composition of claim 10, wherein, upon contact with a cell expressing said Aha gene, the dsRNA inhibits mRNA expression of said Aha gene in said cell by at least 20% compared to a control siRNA duplex unrelated to said Aha gene.

13. The pharmaceutical composition of claim 12, wherein said at least 20% inhibition of mRNA expression of said Aha gene is effected in HeLa and/or MLE12 cells.

14. The pharmaceutical composition of claim 10, wherein the carrier is a lipid carrier.

* * * * *

UNITED STATES PATENT AND TRADEMARK OFFICE
CERTIFICATE OF CORRECTION

| | | |
|---|---|---|
| PATENT NO. | : 7,812,150 B2 | Page 1 of 1 |
| APPLICATION NO. | : 11/750553 | |
| DATED | : October 12, 2010 | |
| INVENTOR(S) | : Rainer Constien et al. | |

It is certified that error appears in the above-identified patent and that said Letters Patent is hereby corrected as shown below:

Title page 1 under "Assignee" section, please add

--THE SCRIPPS RESEARCH INSTITUTE    La Jolla, CA--

Signed and Sealed this
Eleventh Day of September, 2012

David J. Kappos
*Director of the United States Patent and Trademark Office*

SEQUENCE LISTING

<160> NUMBER OF SEQ ID NOS: 217

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
auugguccac ggauaagcut t                                             21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
agcuuauccg uggaccaaut t                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
gugaguaagc uugauggagt t                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
cuccaucaag cuuacucact t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
agucaaaauc cccacuugut t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6 acaaguggggg auuuugacut t                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
aaaucucgug gccuuaaugt t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cauuaaggcc acgagauuut t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
gagauuagug ugagccuugt t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic

```
                                oligonucleotide

<400> SEQUENCE: 10
caaggcucac acuaaucuct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
aaucucgugg ccuuaaugat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
ucauuaaggc cacgagauut t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
agauuagugu gagccuugct t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
gcaaggcuca cacuaaucut t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

<223> OTHER INFORMATION: Description of Artificial Sequence: Synthetic
      oligonucleotide

<400> SEQUENCE: 15
cgggcggacg ccaccaacgt t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
cguugguggc guccgcccgt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
ggcggacgcc accaacguct t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
gacguuggug gcguccgcct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
gggcggacgc caccaacgut t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide

<400> SEQUENCE: 20
acguuggugg cguccgccct t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
caacgucaac aacuggcact t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
gugccaguug uugacguugt t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
gcgggcggac gccaccaact t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
guugguggcg uccgcccgct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
      Synthetic oligonucleotide
<220> FEATURE:
<223> OTHER INFORMATION: Description of Artificial Sequence: Synthetic
      oligonucleotide

<400> SEQUENCE: 25
aucucguggc cuuaaugaat t                                                    21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
uucauuaagg ccacgagaut t                                                    21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
acgucaacaa cuggcacugt t                                                    21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
cagugccagu uguugacgut t                                                    21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
accaacguca acaacuggct t                                                    21

<210> SEQ ID NO 30
<211> LENGTH: 21
<212> TYPE: DNA
<213> ORGANISM: Artificial Sequence
<220> FEATURE:
```

-continued

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
gccaguuguu gacguuggut t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
acgcuggauc guggaggagt t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
cuccuccacg auccagcgut t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
agacccacgc uggaucgugt t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
cacgauccag cgugggucut t                                              21

<210> SEQ ID NO 35
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
gacccacgcu ggaucguggt t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
ccacgaucca gcguggguct t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
gaauuuacau cagcacccut t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
agggugcuga uguaaauuct t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 39
gggaauuuac aucagcacct t                                              21

<210> SEQ ID NO 40
<211> LENGTH: 21
<212> TYPE: DNA
```

-continued

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
ggugcugaug uaaauuccct t                                                    21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
ugggaauuua caucagcact t                                                    21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
gugcugaugu aaauucccat t                                                    21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
ccaacgucaa caacuggcat t                                                    21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
ugccaguugu ugacguuggt t                                                    21

<210> SEQ ID NO 45
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
aaguggggug agggagacct t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
ggucucccuc accccacuut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
acacaaaucu cguggccuut t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
aaggccacga gauuugugut t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
acccacgcug gaucguggat t                                              21

<210> SEQ ID NO 50
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
uccacgaucc agcgugggut t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
gagucaaaau ccccacuugt t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
caagugggga uuuugacuct t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
gagcucuaua gaguguuuat t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
uaaacacucu auagagcuct t                                              21
```

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
ggcagcggua cuacuuugat t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 56
ucaaaguagu accgcugcct t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
gacacaaauc ucguggccut t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
aggccacgag auuuguguct t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
agcgggcgga cgccaccaat t                                              21

```
<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 60
uugguggcgu ccgcccgcut t                                             21

<210> SEQ ID NO 61
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 61 caaaauccccc acuuguaagt t                                            21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 62
cuuacaagug gggauuuugt t                                             21

<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
gagacccacg cuggaucgut t                                             21

<210> SEQ ID NO 64
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 64
acgauccagc gugggucuct t                                             21
```

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 65
gagccuugcc aaagaugagt t                                        21

<210> SEQ ID NO 66
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 66
cucaucuuug gcaaggcuct t                                        21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 67
ugacacaaau cucguggcct t                                        21

<210> SEQ ID NO 68
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 68
ggccacgaga uuugugucat t                                        21

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 69

```
ggagcucuau agaguguuut t                                              21
```

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 70

```
aaacacucua uagagcucct t                                              21
```

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 71

```
cccacgcugg aucguggagt t                                              21
```

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 72

```
cuccacgauc cagcgugggt t                                              21
```

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 73

```
gaucccaau uugucugaut t                                               21
```

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
     Synthetic oligonucleotide
<220> FEATURE:
<223> OTHER INFORMATION: Description of Artificial Sequence: Synthetic
     oligonucleotide

<400> SEQUENCE: 74
aucagacaaa uuggggauct t                                                   21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
gagaucccca auuugucugt t                                                   21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
cagacaaauu ggggaucuct t                                                   21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
agccugacac aaaucucgut t                                                   21

<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 78
acgagauuug ugucaggcut t                                                   21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 79
agauccccaa uuugucugat t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 80
ucagacaaau uggggaucut t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 81
agggagaccc acgcuggaut t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 82
auccagcgug ggucucccut t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 83
gagggagacc cacgcuggat t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 84
uccagcgugg gucucccuct t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 85
gccaaguggg gugagggagt t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
cucccucacc ccacuuggct t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
uggcagcggu acuacuuugt t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 88
caaaguagua ccgcugccat t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

-continued oligonucleotide

<400> SEQUENCE: 89
ugagggagac ccacgcuggt t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 90
ccagcguggg ucucccucat t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
aguggagauu agugugagct t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 92
gcucacacua aucuccacut t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 93
aggagcucua uagaguguut t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
oligonucleotide

<400> SEQUENCE: 94
aacacucuau agagcuccut t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 95
agcgguacua cuuugagggt t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
cccucaaagu aguaccgcut t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 97
cgcuggaucg uggaggagct t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 98
gcuccuccac gauccagcgt t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide

<400> SEQUENCE: 99
gcuggaucgu ggaggagcgt t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 100
cgcuccucca cgauccagct t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 101
cuggaucgug gaggagcggt t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 102
ccgcuccucc acgauccagt t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 103
uggaucgugg aggagcgggt t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
      Synthetic oligonucleotide
<220> FEATURE:
<223> OTHER INFORMATION: Description of Artificial Sequence: Synthetic
      oligonucleotide

<400> SEQUENCE: 104
cccgcuccuc cacgauccat t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 105
gccugacaca aaucucgugt t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 106
cacgagauuu gugucaggct t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 107
ccugacacaa aucucguggt t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 108
ccacgagauu ugugucaggt t                                              21

<210> SEQ ID NO 109
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 109
acgccaccaa cgucaacaat t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 110
uuguugacgu ugguggcgut t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 111
agcucuauag aguguuuact t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 112
guaaacacuc uauagagcut t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 113
gggcuggcag cgguacuact t                                              21

<210> SEQ ID NO 114
<211> LENGTH: 21
<212> TYPE: DNA
<213> ORGANISM: Artificial Sequence
```

-continued

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 114
guaguaccgc ugccagccct t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 115
cuggcagcgg uacuacuuut t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 116
aaaguaguac cgcugccagt t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 117
ggaugaagug gagauuagut t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 118
acuaaucucc acuucaucct t                                              21

<210> SEQ ID NO 119
<211> LENGTH: 21
<212> TYPE: DNA
```

<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 119
accagaggag cucuauagat t                                             21

<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 120
ucuauagagc uccucuggut t                                             21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 121
aaguggagau uagugugagt t                                             21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 122
cucacacuaa ucuccacuut t                                             21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 123
gaggagcucu auagagugut t                                             21

<210> SEQ ID NO 124
<211> LENGTH: 21

-continued

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 124
acacucuaua gagcuccuct t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 125
gggagaccca cgcuggauct t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 126
gauccagcgu gggucuccct t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 127
ugagccugac acaaaucuct t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 128
gagauuugug ucaggcucat t                                              21

<210> SEQ ID NO 129
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 129
gcggacgcca ccaacgucat t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 130
ugacguuggu ggcguccgct t                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 131
cggacgccac caacgucaat t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 132
uugacguugg uggcguccgt t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 133
gaaguggaga uuagugugat t                                              21
```

```
<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 134
ucacacuaau cuccacuuct t                                             21

<210> SEQ ID NO 135
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 135
cucguggccu uaaugaaggt t                                             21

<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 136
ccuucauuaa ggccacgagt t                                             21

<210> SEQ ID NO 137
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 137
ucguggccuu aaugaaggat t                                             21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 138
uccuucauua aggccacgat t                                             21
```

```
<210> SEQ ID NO 139
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 139
aaugggaauu uacaucagct t                                           21

<210> SEQ ID NO 140
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 140
gcugauguaa auucccauut t                                           21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 141
ggaauuuaca ucagcaccct t                                           21

<210> SEQ ID NO 142
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 142
gggugcugau guaaauucct t                                           21

<210> SEQ ID NO 143
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 143
ggagauuagu gugagccuut t                                           21
```

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 144
aaggcucaca cuaaucucct t                                                 21

<210> SEQ ID NO 145
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 145
cacaaaucuc guggccuuat t                                                 21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 146
uaaggccacg agauuugugt t                                                 21

<210> SEQ ID NO 147
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 147
acaaaucucg uggccuuaat t                                                 21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 148
uuaaggccac gagauuugut t 21

```
<210> SEQ ID NO 149
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 149
```
ggagacccac gcuggaucgt t 21

```
<210> SEQ ID NO 150
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 150
```
cgauccagcg ugggucucct t 21

```
<210> SEQ ID NO 151
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 151
```
ggacgccacc aacgucaact t 21

```
<210> SEQ ID NO 152
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 152
```
guugacguug guggcgucct t 21

```
<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
```

-continued gaugaagugg agauuagugt t					21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154
cacuaaucuc cacuucauct t					21

<210> SEQ ID NO 155
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 155
gugagccuug ccaaagaugt t					21

<210> SEQ ID NO 156
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 156
caucuuuggc aaggcucact t					21

<210> SEQ ID NO 157
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 157
caaugaaugg agagucagut t					21

<210> SEQ ID NO 158
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide -continued

<400> SEQUENCE: 158
acugacucuc cauucauugt t                                            21

<210> SEQ ID NO 159
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 159
auuaguguga gccuugccat t                                            21

<210> SEQ ID NO 160
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 160
uggcaaggcu cacacuaaut t                                            21

<210> SEQ ID NO 161
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 161
agaugagccu gacacaaaut t                                            21

<210> SEQ ID NO 162
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 162
auuuguguca ggcucaucut t                                            21

<210> SEQ ID NO 163
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide -continued

```
<400> SEQUENCE: 163
uagugugagc cuugccaaat t                                             21

<210> SEQ ID NO 164
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 164
uuuggcaagg cucacacuat t                                             21

<210> SEQ ID NO 165
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 165
uuugccacca ucaccuugat t                                             21

<210> SEQ ID NO 166
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 166
ucaaggugau gguggcaaat t                                             21

<210> SEQ ID NO 167
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 167
acggagagag augcuucaat t                                             21

<210> SEQ ID NO 168
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

-continued oligonucleotide

<400> SEQUENCE: 168
uugaagcauc ucucuccgut t                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 169
cggagagaga ugcuucaaat t                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 170
uuugaagcau cucucuccgt t                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 171
aaaaucccca cuuguaagat t                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 172
ucuuacaagu ggggauuuut t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
      oligonucleotide

<400> SEQUENCE: 173
auccccaauu ugucugaugt t                                                 21

<210> SEQ ID NO 174
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 174
caucagacaa auuggggaut t                                                 21

<210> SEQ ID NO 175
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 175
ucaaaauccc cacuuguaat t                                                 21

<210> SEQ ID NO 176
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 176
uuacaagugg ggauuuugat t                                                 21

<210> SEQ ID NO 177
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 177
aaauccccac uuguaagaut t                                                 21

<210> SEQ ID NO 178
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide -continued

```
<220> FEATURE:
<223> OTHER INFORMATION: Description of Artificial Sequence: Synthetic
      oligonucleotide

<400> SEQUENCE: 178
aucuuacaag ugggauuut t                                                  21

<210> SEQ ID NO 179
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 179
uccccaauuu gucugaugat t                                                 21

<210> SEQ ID NO 180
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 180
ucaucagaca aauuggggat t                                                 21

<210> SEQ ID NO 181
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 181
auggccaagu ggggugaggt t                                                 21

<210> SEQ ID NO 182
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 182
ccucacccca cuuggccaut t                                                 21

<210> SEQ ID NO 183
<211> LENGTH: 21
<212> TYPE: DNA
<213> ORGANISM: Artificial Sequence
<220> FEATURE:
<223> OTHER INFORMATION: Description of Combined DNA/RNA Molecule:
```

Synthetic oligonucleotide
<220> FEATURE:
<223> OTHER INFORMATION: Description of Artificial Sequence: Synthetic
      oligonucleotide

<400> SEQUENCE: 183
ggagucaaaa uccccacuut t                                               21

<210> SEQ ID NO 184
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 184 aagugggau uuugacucct t                                                21

<210> SEQ ID NO 185
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
gatgtaaatt cccattgctt ctcttttttc tcttggaaag aaagt                     45

<210> SEQ ID NO 186
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
tgaactctgt tttgagggtg ctttttttctc ttggaaagaa agt                      43

<210> SEQ ID NO 187
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
gggtctactg actctccatt cattgttttt ctcttggaaa gaaagt                    46

<210> SEQ ID NO 188
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
ccttgcgctc ctcagttttc tttttctctt ggaaagaaag t                         41

<210> SEQ ID NO 189

-continued

```
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
ggtttttgaa ggagcaggct tagttttttct cttggaaaga aagt                      44

<210> SEQ ID NO 190
<211> LENGTH: 47
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
acgctgtttt catcagacaa attttttttag gcataggacc cgtgtct                   47

<210> SEQ ID NO 191
<211> LENGTH: 49
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
gctcacacta atctccactt catccttttt aggcatagga cccgtgtct                  49

<210> SEQ ID NO 192
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
tcattaaggc cacgagattt gttttttagg cataggaccc gtgtct                     46

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
taggtaagat catgccctgg gtttttaggc ataggacccg tgtct                      45

<210> SEQ ID NO 194
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
actccaacag gtctggcctg tttttaggca taggacccgt gtct                       44

<210> SEQ ID NO 195
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
gtcaggctca tctttggcaa g                                              21

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
tagaagtttc acccttcttt cct                                            23

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
agtgctggct gccccact                                                  18

<210> SEQ ID NO 198
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
ctcgaacggc caggaacatt tttctcttgg aaagaaagt                           39

<210> SEQ ID NO 199
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
gcacttgccc tcttcatttt ctattttct cttggaaaga aagt                      44

<210> SEQ ID NO 200
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
ttgatggatg cctccccatt ttttctcttg gaaagaaagt                          40

<210> SEQ ID NO 201
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 201
aactctgtct tgagggtgct gattttttct cttggaaaga aagt              44

<210> SEQ ID NO 202
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
tttggcctgg cttttttgaat ttttctcttg gaaagaaagt                  40

<210> SEQ ID NO 203
<211> LENGTH: 49
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
caagcttgtt cacttcggtc acctctttt aggcatagga cccgtgtct          49

<210> SEQ ID NO 204
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
cctgacttag aggtacctgt ccagtttttt taggcatagg acccgtgtct        50

<210> SEQ ID NO 205
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
gatttccaca tgtcctttgt actgcacttt tttaggcata ggacccgtgt ct     52

<210> SEQ ID NO 206
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
attttcatca gacaaattgg gttttaggc ataggacccg tgtct              45

<210> SEQ ID NO 207
<211> LENGTH: 46
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 207
taatctccac ttcatccacg cttttttagg cataggaccc gtgtct                        46

<210> SEQ ID NO 208
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
tttcaccccg tcttccttca tttttaggca taggacccgt gtct                          44

<210> SEQ ID NO 209
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
actgtgggca agatcatgcc ctgagtattt ttaggcatag gacccgtgtc t                  51

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
aagataagtt tgcctttcct gttg                                                24

<210> SEQ ID NO 211
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
cagtttgatg gtccactcat agaag                                               25

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
catctttggc aaggctcaca c                                                   21

<210> SEQ ID NO 213
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 213
ttaaggccac gagatttgtg tcaggct                                              27

<210> SEQ ID NO 214
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
gtaaattccc actgcttctc tcagaag                                              27

<210> SEQ ID NO 215
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
cactggatct actgactctc cattc                                                25

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
ctcagtcttt agtgctggct ggcc                                                 24

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
ggagcagact tagccttgca agt                                                  23
```